United States Patent
Goetz et al.

(10) Patent No.: US 8,996,123 B2
(45) Date of Patent: Mar. 31, 2015

(54) MANAGING ELECTRICAL STIMULATION THERAPY BASED ON VARIABLE ELECTRODE COMBINATIONS

(75) Inventors: Steven M. Goetz, North Oaks, MN (US); Jon P. Davis, St. Michael, MN (US); Nathan A. Torgerson, Andover, MN (US); Shyam Gokaldas, New Brighton, MN (US); Ashish Singal, Blaine, MN (US); Rajeev M. Sahasrabudhe, Maple Grove, MN (US); Brent A. Huhta, Big Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 43 days.

(21) Appl. No.: 12/906,418

(22) Filed: Oct. 18, 2010

(65) Prior Publication Data
US 2011/0093030 A1    Apr. 21, 2011

Related U.S. Application Data

(60) Provisional application No. 61/253,759, filed on Oct. 21, 2009, provisional application No. 61/260,644, filed on Nov. 12, 2009.

(51) Int. Cl.
*A61N 1/36* (2006.01)
*A61N 1/372* (2006.01)
*A61N 1/05* (2006.01)

(52) U.S. Cl.
CPC .......... *A61N 1/37247* (2013.01); *A61N 1/0553* (2013.01)
USPC ............................... 607/59; 607/17; 607/117

(58) Field of Classification Search
USPC .................................................... 607/59, 17
See application file for complete search history.

(56) References Cited

U.S. PATENT DOCUMENTS

| | | | |
|---|---|---|---|
| 4,592,359 A | 6/1986 | Galbraith |
| 4,931,795 A | 6/1990 | Gord |
| 5,190,035 A | 3/1993 | Salo et al. |

(Continued)

FOREIGN PATENT DOCUMENTS

| | | |
|---|---|---|
| EP | 2039391 A1 | 3/2009 |
| WO | 0154579 A1 | 8/2001 |

(Continued)

OTHER PUBLICATIONS

Reply to Written Opinion for corresponding patent application No. PCT/US2010/053148, filed Aug. 17, 2011, 26 pages.

(Continued)

*Primary Examiner* — Carl H Layno
*Assistant Examiner* — Jennifer Ghand
(74) *Attorney, Agent, or Firm* — Shumaker & Sieffert Medtronic, Inc.

(57) ABSTRACT

Various programming techniques are described for medical devices that deliver electrical stimulation therapy that may include mapping between discrete electrical stimulation parameters and a graphical view of the electrical stimulation representing a stimulation zone generated by the parameters. In one example, a method includes receiving, via a programmer for an electrical stimulator, user input that graphically manipulates at least one of size and a shape of a graphical representation of at least one electrical stimulation zone displayed on the programmer, and defining a program to control delivery of electrical stimulation therapy based on the user input.

63 Claims, 22 Drawing Sheets

(56) References Cited

U.S. PATENT DOCUMENTS

| | | | |
|---|---|---|---|
| 5,241,472 A | 8/1993 | Gur et al. |
| 5,501,703 A | 3/1996 | Holsheimer et al. |
| 5,713,922 A | 2/1998 | King |
| 5,776,172 A | 7/1998 | Schulman et al. |
| 5,800,465 A | 9/1998 | Thompson et al. |
| 5,895,416 A | 4/1999 | Barreras, Sr. et al. |
| 5,916,238 A | 6/1999 | Hauser et al. |
| 5,954,758 A | 9/1999 | Peckham et al. |
| 6,341,234 B1 | 1/2002 | Thong et al. |
| 6,393,325 B1 | 5/2002 | Mann et al. |
| 6,421,564 B1 | 7/2002 | Yerich et al. |
| 6,505,078 B1 | 1/2003 | King et al. |
| 6,516,227 B1 | 2/2003 | Meadows et al. |
| 6,587,724 B2 | 7/2003 | Mann |
| 6,609,032 B1 | 8/2003 | Woods et al. |
| 6,625,482 B1 | 9/2003 | Panescu et al. |
| 6,799,070 B2 | 9/2004 | Wolfe et al. |
| 6,853,863 B2 | 2/2005 | Carter et al. |
| 6,895,280 B2 | 5/2005 | Meadows et al. |
| 6,909,917 B2 | 6/2005 | Woods et al. |
| 7,035,690 B2 | 4/2006 | Goetz |
| 7,127,297 B2 | 10/2006 | Law et al. |
| 7,174,210 B1 | 2/2007 | Levine |
| 7,180,760 B2 | 2/2007 | Varrichio et al. |
| 7,216,001 B2 | 5/2007 | Hacker et al. |
| 7,251,529 B2 | 7/2007 | Greenwood-Van Meerveld |
| 7,271,663 B2 | 9/2007 | Baum et al. |
| 7,317,948 B1 | 1/2008 | King et al. |
| 7,386,348 B2 | 6/2008 | North et al. |
| 7,387,603 B2 | 6/2008 | Gross et al. |
| 7,389,147 B2 | 6/2008 | Wahlstrand et al. |
| 7,463,928 B2 | 12/2008 | Lee et al. |
| 7,477,723 B2 | 1/2009 | Kamegawa et al. |
| 7,505,809 B2 | 3/2009 | Strommer et al. |
| 7,519,428 B1 | 4/2009 | Palmer |
| 7,519,431 B2 | 4/2009 | Goetz et al. |
| 7,522,962 B1 | 4/2009 | Doron et al. |
| 7,526,341 B2 | 4/2009 | Goetz et al. |
| 7,567,834 B2 | 7/2009 | Clayton et al. |
| 7,571,007 B2 | 8/2009 | Erickson et al. |
| 7,623,918 B2 | 11/2009 | Goetz |
| 7,768,151 B2 | 8/2010 | Andreu et al. |
| 7,974,697 B2 | 7/2011 | Maschino et al. |
| 2004/0059395 A1 | 3/2004 | North et al. |
| 2004/0098063 A1 | 5/2004 | Goetz |
| 2004/0210273 A1 | 10/2004 | Wang |
| 2004/0267330 A1 | 12/2004 | Lee et al. |
| 2005/0065556 A1 | 3/2005 | Reghabi et al. |
| 2005/0131464 A1 | 6/2005 | Heinrich et al. |
| 2006/0178706 A1 | 8/2006 | Lisogurski et al. |
| 2006/0195145 A1 | 8/2006 | Lee et al. |
| 2006/0229687 A1 | 10/2006 | Goetz et al. |
| 2006/0241720 A1 | 10/2006 | Woods et al. |
| 2006/0259079 A1 | 11/2006 | King |
| 2006/0259099 A1 | 11/2006 | Goetz et al. |
| 2006/0293609 A1 | 12/2006 | Stahmann et al. |
| 2007/0100408 A1 | 5/2007 | Gerber et al. |
| 2007/0203537 A1* | 8/2007 | Goetz et al. ............ 607/59 |
| 2007/0203540 A1 | 8/2007 | Goetz et al. |
| 2007/0203541 A1 | 8/2007 | Goetz et al. |
| 2007/0203542 A1 | 8/2007 | Goetz et al. |
| 2007/0203544 A1 | 8/2007 | Goetz et al. |
| 2007/0203546 A1 | 8/2007 | Stone et al. |
| 2008/0004674 A1 | 1/2008 | King et al. |
| 2008/0046036 A1 | 2/2008 | King et al. |
| 2008/0071324 A1 | 3/2008 | Miesel et al. |
| 2008/0082137 A1 | 4/2008 | Kieval et al. |
| 2008/0109048 A1 | 5/2008 | Moffitt |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0215118 A1 | 9/2008 | Goetz et al. |
| 2008/0215119 A1 | 9/2008 | Woods et al. |
| 2008/0221637 A1 | 9/2008 | Woods et al. |
| 2008/0288023 A1 | 11/2008 | John |
| 2008/0294211 A1 | 11/2008 | Moffitt |
| 2009/0018617 A1 | 1/2009 | Skelton et al. |
| 2009/0024189 A1 | 1/2009 | Lee et al. |
| 2009/0149917 A1 | 6/2009 | Whitehurst et al. |
| 2010/0023069 A1 | 1/2010 | Moffitt et al. |
| 2010/0023070 A1 | 1/2010 | Moffitt et al. |
| 2010/0106219 A1 | 4/2010 | Torgerson et al. |
| 2011/0093044 A1 | 4/2011 | Moffitt |
| 2011/0313268 A1 | 12/2011 | Kokones et al. |

FOREIGN PATENT DOCUMENTS

| | | | |
|---|---|---|---|
| WO | 2009076211 A1 | 6/2009 |
| WO | 2009134480 A1 | 11/2009 |
| WO | 2009137121 A1 | 11/2009 |
| WO | 2010011721 A1 | 1/2010 |

OTHER PUBLICATIONS

Written Opinion of international application No. PCT/US2010/053148, dated Jan. 30, 2012, 9 pp.

Office Action from U.S. Appl. No. 12/769,149, dated Sep. 26, 2011, 21 pp.

Response to Office Action dated Sep. 26, 2011, from U.S. Appl. No. 12/769,149, filed Dec. 19, 2011, 21 pp.

U.S. Appl. No. 12/696,988, by Nathan A. Torgerson, filed Jan. 29, 2010.

U.S. Appl. No. 12/696,992, by Nathan A. Torgerson, filed Jan. 29, 2010.

U.S. Appl. No. 12/769,149, by Nathan A. Torgerson, filed Apr. 28, 2010.

U.S. Appl. No. 12/829,089, by Nathan A. Torgerson, filed Jul. 1, 2010.

U.S. Appl. No. 61/353,842, by Steven M. Goetz, filed Jun. 11, 2010.

U.S. Appl. No. 12/829,108, by Steven M. Goetz, filed Jul. 1, 2010.

Lee et al., "AIM Targeting Technique: A Novel Method of Focusing the Volume of Activation on the Dorsal Column with Multiple Independent Current Control in a Computational Model," Boston Scientific Neuromodulation, Valencia, California, presented at 13th North American Neuromodulation Society Annual Meeting, Las Vegas, Nevada, Dec. 3-6, 2009, Poster ID A107, 2 pp.

International Search Report and Written Opinion of international application No. PCT/2010/053148, dated Jan. 26, 2011, 14 pp.

Notification of Transmittal of the International Preliminary Report on Patentability for patent application No. PCT/US2010/053148, mailed Apr. 25, 2012, 22 pages.

Bourret et al., Programmable High-Amplitude Balanced Stimulus Current—Source for Implantable Microstimulators, Proceedings of the 19th Annual International Conference of the IEEE Engineering in Medicine and Biology Society, Oct. 30-Nov. 2, 1997, pp. 1938-1941.

Kim et al., A 64-Site Multishank CMOS Low-Profile Neural Stimulation Probe, IEEE Journal of Solid State Circuits, vol. 31, No. 9, Sep. 1996, pp. 1230-1238.

St-Amand et al., Design and Optimization of a Low DC Offset CMOS Current—Source Dedicated to Implantable Miniaturized Stimulators, Analog Integrated Circuits and Signal Processing, vol. 11, pp. 47-61 (1996).

Office Action from U.S. Appl. No. 12/769,149, Jul. 27, 2012, 8 pp.

Office Action from U.S. Appl. No. 12/696,992, dated Sep. 13, 2012, 6 pp.

Office Action from U.S. Appl. No. 13/156,011, dated Sep. 21, 2012, 11 pp.

Bian et al., "Double electrodes simultaneous stimulation and implantation technique in deep brain stimulation," Chin J Traumatol 8(4):253-256, Aug. 2005 (English translation of abstract only).

Office Action from U.S. Appl. No. 12/829,108, dated Sep. 17, 2012, 34 pp.

Office Action from U.S. Appl. No. 12/829,089, dated Oct. 17, 2012, 29 pp.

Response to Final Office Action dated Jan. 16, 2014 and to Advisory Action dated Apr. 23, 2014, from U.S. Appl. No. 12/769,149, filed May 21, 2014, 23 pp.

Office Action from U.S. Appl. No. 12/696,988, dated Dec. 14, 2010, 26 pp.

(56) References Cited

OTHER PUBLICATIONS

Response to Office Action dated Sep. 13, 2012, from U.S. Appl. No. 12/696,992, filed Dec. 10, 2012, 14 pp.
Response to Office Action dated Jul. 27, 2012, from U.S. Appl. No. 12/769,149, filed Nov. 20, 2012, 18 pp.
Response to Office Action dated Oct. 17, 2012, from U.S. Appl. No. 12/829,089, filed Dec. 18, 2012, 16 pp.
Response to Office Action dated Sep. 21, 2012, from U.S. Appl. No. 13/156,011, filed Dec. 21, 2012, 15 pp.
Response to Office Action dated Sep. 17, 2012, from U.S. Appl. No. 12/829,108, filed Dec. 14, 2012, 24 pp.
Office Action from U.S. Appl. No. 12/829,108, dated Jan. 9, 2013, 33 pp.
Office Action from U.S. Appl. No. 12/696,992, dated Jan. 9, 2013, 5 pp.
Final Office Action from U.S. Appl. No. 12/769,149, dated Jan. 16, 2014, 9 pp.
Office action for U.S. Appl. No. 13/156,011, mailed Mar. 5, 2013, 14 pages.
Response to office action for U.S. Appl. No. 12/829,089, filed Apr. 2, 2013, 17 pages.
Office Action from U.S. Appl. No. 12/829,089, dated Jan. 28, 2013, 30 pp.
Response to Final Office Action dated Jan. 16, 2014, from U.S. Appl. No. 12/769,149, filed Mar. 17, 2014, 8 pp.
Office Action from U.S. Appl. No. 12/769,149, dated Jul. 12, 2013, 11 pp.
Notice of Allowance from U.S. Appl. No. 12/829,089, dated May 15, 2013, 3 pp.
PTO-892 form from U.S. Appl. No. 12/829,089 dated Aug. 28, 2013, 3 pp.
Response to Final Office Action dated Jul. 12, 2013, from the U.S. Appl. No. 12/769,149, filed Sep. 12, 2013, 9 pp.
Notice of Allowance from U.S. Appl. No. 13/156,011, dated Jun. 13, 2013, 13 pp.

\* cited by examiner

MANAGING ELECTRICAL STIMULATION THERAPY BASED ON VARIABLE ELECTRODE COMBINATIONS

This application claims the benefit of U.S. Provisional Application No. 61/253,759, entitled, "MANAGING ELECTRICAL STIMULATION THERAPY BASED ON VARIABLE ELECTRODE COMBINATIONS," by Steven Goetz, Jon Davis, Nathan Torgerson, Shyam Gokaldas, Ashish Singal, and Rajeev Sahasrabudhe, and filed on Oct. 21, 2009; and U.S. Provisional Application No. 61/260,644, entitled, "MANAGING ELECTRICAL STIMULATION THERAPY BASED ON VARIABLE ELECTRODE COMBINATIONS," by Steven Goetz, Jon Davis, Nathan Torgerson, Shyam Gokaldas, Ashish Singal, and Rajeev Sahasrabudhe, and filed on Nov. 12, 2009, the entire contents of each being incorporated herein by reference.

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a current or voltage pulse amplitude, pulse width and pulse rate. A set of parameter values may be referred to as a stimulation program. A program group may include multiple programs. Multiple programs in a program group may be delivered on a simultaneous, time-interleaved, or overlapping basis.

SUMMARY

In general, this disclosure describes programming techniques, for medical devices that deliver electrical stimulation therapy, that may include mapping between discrete electrical stimulation parameters and a graphical view of the electrical stimulation representing a stimulation zone generated by the parameters, including details regarding dynamic behavior of such a system as parameters are changed or stimulation parameter limits or stimulation zone boundaries are reached. In some cases, such limits or boundaries may be defined as stimulation interlocks that constrain programming options. Stimulation interlocks may be combinations of parameters that are mutually exclusive, either because the device cannot achieve them or because achieving them would be hazardous or otherwise therapeutically undesirable.

In one example, the disclosure is directed to a programmer for an electrical stimulator, the programmer comprising a user interface that displays a graphical representation of at least one electrical stimulation zone and receives user input graphically manipulating at least one of a size and a shape of the representation of the at least one electrical stimulation zone, and a processor configured to define a program to control delivery of electrical stimulation therapy by a stimulator based on the user input, wherein the processor is further configured to define, without user intervention, at least one electrode on at least one lead to deliver at least a portion of the electrical stimulation therapy, and determine, without user intervention, an electrical stimulation contribution of the at least one defined electrode to the at least one stimulation zone.

In another example, the disclosure is directed to a method comprising receiving, via a programmer for an electrical stimulator, user input that graphically manipulates at least one of a size and a shape of a graphical representation of at least one electrical stimulation zone displayed on the programmer, and defining a program to control delivery of electrical stimulation therapy based on the user input, wherein defining the program comprises defining, without user intervention, at least one electrode on at least one lead to deliver at least a portion of the electrical stimulation therapy, and determining, without user intervention, an electrical stimulation contribution of the at least one defined electrode to the at least one stimulation zone.

In another example, the disclosure is directed to a programmer for an electrical stimulator, the programmer comprising means for receiving, via a programmer for an electrical stimulator, user input that graphically manipulates at least one of a size and a shape of a graphical representation of at least one electrical stimulation zone displayed on the programmer, and means for defining a program to control delivery of electrical stimulation therapy based on the user input, wherein the means for defining the program comprises means for defining, without user intervention, at least one electrode on at least one lead to deliver at least a portion of the electrical stimulation therapy, and means for determining, without user intervention, an electrical stimulation contribution of the at least one defined electrode to the at least one stimulation zone.

In another example, the disclosure is directed to a computer-readable medium comprising instructions that, upon execution, cause a processor in programmer for an electrical stimulator to receive user input graphically manipulating at least one of a size and a shape of a graphical representation of at least one electrical stimulation zone displayed on the programmer, and define a program to control delivery of electrical stimulation therapy based on the user input wherein the instructions that cause the processor to define the program comprise instructions that cause the processor to define, without user intervention, at least one electrode on at least one lead to deliver at least a portion of the electrical stimulation therapy, and determine, without user intervention, an electrical stimulation contribution of the at least one defined electrode to the at least one stimulation zone.

In another example, the disclosure is directed to a system comprising an implantable medical device (IMD) configured to deliver electrical stimulation therapy to a patient, a user interface that displays a graphical representation of at least one electrical stimulation zone and receives user input graphically manipulating at least one of a size and a shape of the representation of the at least one electrical stimulation zone, and a processor configured to define a program to control delivery of electrical stimulation therapy by a stimulator based on the user input, wherein the processor is further configured to define, without user intervention, at least one electrode on at least one lead to deliver at least a portion of the electrical stimulation therapy, and determine, without user intervention, an electrical stimulation contribution of the at least one defined electrode to the at least one stimulation zone.

In another example, the disclosure is directed to a programmer for an implantable electrical stimulator. The programmer comprises a user interface that receives user input, the user input comprising graphically defining at least one electrical stimulation zone for at least one region of a patient. The programmer further comprises a processor that defines a program to control delivery of electrical stimulation therapy by implantable electrical stimulator elements to at least one region of a patient based on the user input, wherein the processor is configured to combine an anatomical representation of the at least one region with at least one image of the elements.

In another example, the disclosure is directed to a method comprising receiving user input that graphically defines at least one electrical stimulation zone for at least one region of a patient, combining an anatomical representation of the at least one region with at least one image of implantable electrical stimulator elements, and defining a program to control delivery of electrical stimulation therapy by the implantable electrical stimulator elements to the at least one region based on the user input.

In another example, the disclosure is directed to a device comprising means for receiving user input that graphically defines at least one electrical stimulation zone for at least one region of a patient, means for combining an anatomical representation of the at least one region with at least one image of implantable electrical stimulator elements, and means for defining a program to control delivery of electrical stimulation therapy by the implantable electrical stimulator elements to the at least one region based on the user input.

In another example, the disclosure is directed to a computer-readable medium comprising instructions that, upon execution, cause a processor to receive user input that graphically defines at least one electrical stimulation zone for at least one region of a patient, combine an anatomical representation of the at least one region with at least one image of implantable electrical stimulator elements, and define a program to control delivery of electrical stimulation therapy by the implantable electrical stimulator elements to the at least one region based on the user input.

The details of one or more aspects of the disclosure are set forth in the accompanying drawings and the description below. Other features, objects, and advantages will be apparent from the description and drawings, and from the claims.

DETAILED DESCRIPTION

In zone-based programming, a user may graphically define a desired stimulation field(s) within zones on or adjacent to one or more leads, and a programmer may generate the stimulation parameters required to create the stimulation field. This disclosure describes techniques for translating one or more user input defined stimulation zones into a set of dynamically configurable electrodes recruited for delivering electrical stimulation therapy to a patient, determining the variable electrical stimulation contributions of each electrode to the stimulation or shielding zone, and determining amplitudes of electrical stimulation associated with and delivered by the electrodes when using zone-based programming. Also described are techniques for graphically representing the stimulation zone and permitting a user to manipulate the shape and position of the zone to cover multiple pain areas or dermatomes, including behaviors of the zone while moving and when colliding with other zones or violating system interlocks such as zone limits or boundaries.

Figure 1:
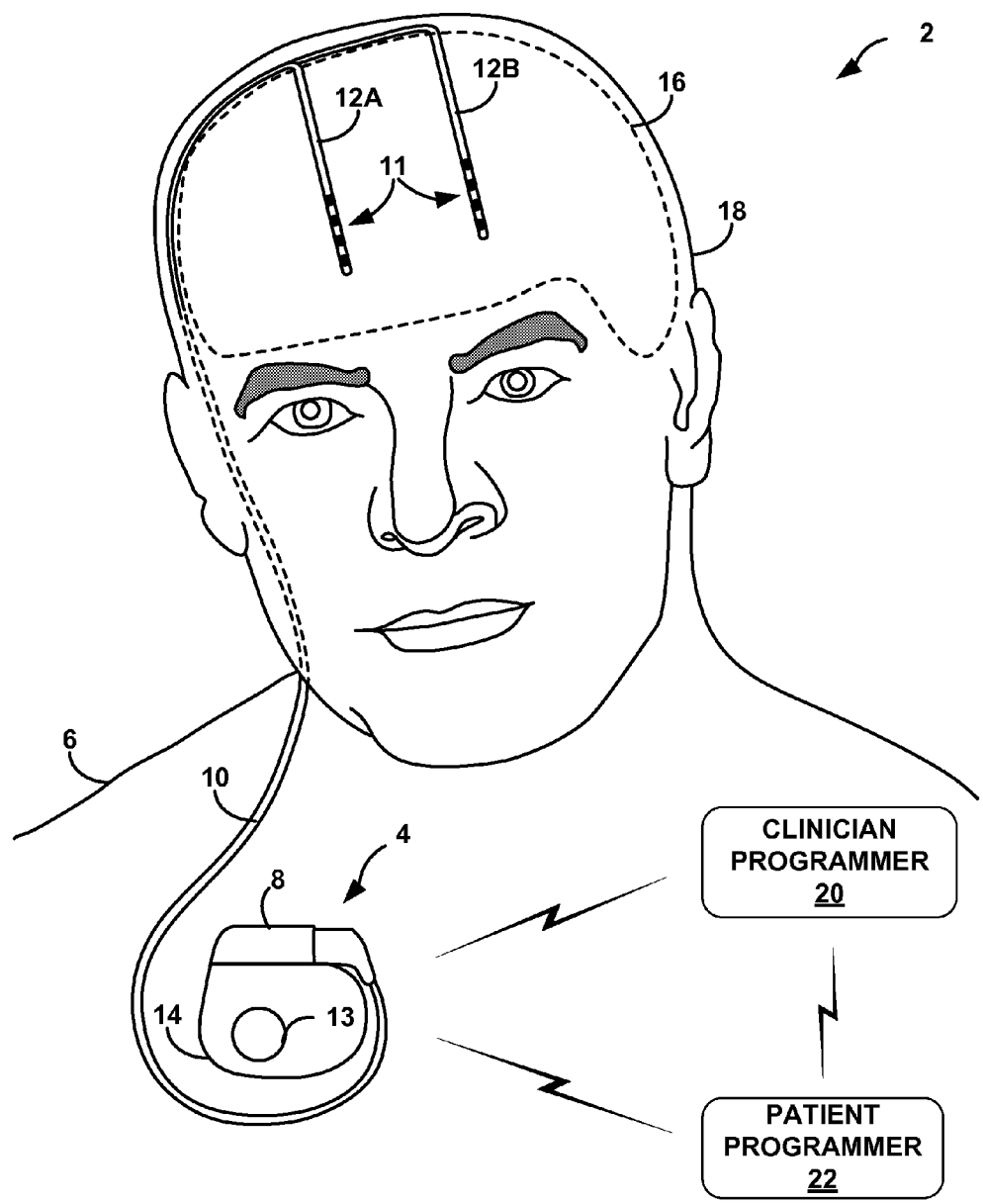
FIG. 1 is a conceptual diagram illustrating an example therapy system that includes an implantable stimulator coupled to a stimulation lead.

FIG. 1 is a conceptual diagram illustrating an example system 2 that may be used to deliver stimulation therapy to patient 6. Patient 6 ordinarily, but not necessarily, will be a human. Generally, therapy system 2 includes implantable stimulator 4 that delivers electrical stimulation to patient 6 via one or more implantable electrodes (not shown). The implantable electrodes may be deployed on one or more implantable medical leads, such as implantable medical lead 10, and in some cases on a can electrode. The electrical stimulation may be in the form of controlled current pulses or voltage pulses, or substantially continuous current or voltage waveforms. Various parameters of the pulses or waveforms may be defined by a stimulation program. The pulses or waveforms may be delivered substantially continuously or in bursts, segments, or patterns, and may be delivered alone or in combination with pulses or waveforms defined by one or more other stimulation programs. Although FIG. 1 shows a fully implantable stimulator 4, techniques described in this disclosure may be applied to external stimulators having electrodes deployed via percutaneously implantable leads. In some example implementations, one or more of the electrodes may be located on a housing 14, i.e., "can" or "case," of the implantable stimulator 4. In addition, in some cases, implantable electrodes may be deployed on a leadless stimulator.

In the example illustrated in FIG. 1, implantable stimulator 4 is implanted within a subcutaneous pocket in a clavicle region of patient 6. Stimulator 4 generates programmable electrical stimulation, e.g., a current or voltage waveform or current or voltage pulses, and delivers the stimulation via an implantable medical lead 10 carrying an array of implantable stimulation electrodes 11. In general, delivery of electrical stimulation using controlled current pulses will be described in this disclosure for purposes of illustration. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, or sixteen electrodes. In FIG. 1, each lead segment 12A, 12B carries four electrodes, configured as ring electrodes at different axial positions near the distal ends of the lead segments. Throughout the remainder of this disclosure, for purposes of simplicity, the disclosure may generally refer to electrodes carried on "leads" rather than "lead segments."

A unipolar stimulation arrangement generally refers to the use of an anode on the housing that sources current and one or more cathodes on one or more leads that sink current. A bipolar stimulation arrangement generally refers to the use of an anode on a lead that sources current and a cathode on the same lead and/or another lead that sinks current. A multipolar stimulation arrangement generally refers to the use of more than one anode on a lead that each source current and one or more cathodes on the same lead or another lead that sink current, or the use of one anode on a lead that sources current and multiple cathodes on the same lead or another lead that sink current. A hybrid stimulation arrangement that combines both unipolar and bipolar electrode relationships may be referred to as an omnipolar arrangement. Techniques of this disclosure may be implemented using unipolar arrangements, bipolar/multipolar arrangements, and omnipolar arrangements.

FIG. 1 further depicts a housing, or can, electrode 13. Housing electrode 13 may be formed integrally with an outer surface of hermetically-sealed housing 14 of implantable stimulator 4, also referred to in this disclosure as implantable medical device (IMD) 4, or otherwise coupled to housing 14. In one example, housing electrode 13 may be described as an active, non-detachable electrode on the surface of the IMD. In some examples, housing electrode 13 is defined by an uninsulated portion of an outward facing portion of housing 14 of IMD 4. Other divisions between insulated and uninsulated portions of housing 14 may be employed to define two or more housing electrodes, which may be referred to as case or can electrodes. In some examples, housing electrode 13 comprises substantially all of housing 14, one side of housing 14, a portion of housing 14, or multiple portions of housing 14. In one example implementation of the techniques of this disclosure, e.g., an omnipolar arrangement, one or more electrodes 11 may transfer stimulation pulses from the lead 10 to the tissue substantially simultaneously with stimulation pulses delivered via housing electrode 13.

In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator 4 may be coupled to one or more leads which may or may not be bifurcated. In such examples, the leads may be coupled to implantable stimulator 4 via a common lead extension or via separate lead extensions.

A proximal end of lead 10 may be both electrically and mechanically coupled to header 8 on implantable stimulator 4 either directly or indirectly via a lead extension. Conductors in the lead body may electrically connect stimulation electrodes located on lead segments 12 to implantable stimulator 4. Lead 10 traverses from the implant site of implantable stimulator 4 along the neck of patient 6 to cranium 18 of patient 6 to access brain 16. Lead segments 12A and 12B are implanted within the right and left hemispheres, respectively, in order to deliver electrical stimulation to one more regions of brain 16, which may be selected based on the patient condition or disorder.

Implantable stimulator 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder and movement disorders, such as Parkinson's disease, spasticity, epilepsy, and dystonia. DBS also may be useful for treating other patient conditions, such as migraines and obesity. However, the disclosure is not limited to the configuration of lead 10 shown in FIG. 1, or to the delivery of DBS or CS therapy.

Lead segments 12A, 12B may be implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment. Example locations for lead segments 12A, 12B within brain 26 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, lead segments 12 may be implanted to provide stimulation to the visual cortex of brain 16 or occipital nerves in order to reduce or eliminate migraine headaches afflicting patient 6. However, the target therapy delivery site may depend upon the patient condition or disorder being treated.

The electrodes of lead segments 12A, 12B are shown as ring electrodes. Ring electrodes are commonly used in DBS applications because they are simple to program and are capable of delivering an electrical field to any tissue adjacent to lead segments 12A, 12B. In other implementations, the electrodes of lead segments 12A, 12B may have different configurations. For example, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, lead segments 12 may have shapes other than elongated cylinders as shown in FIG. 1. For example, lead segments 12 may be paddle leads, spherical leads, bendable leads, or any other type of shape effective in treating patient 6.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust electrical stimulation therapy. In particular, patient programmer 22 may permit patient 6 to adjust stimulation parameters of a program such as duration, current or voltage amplitude, pulse width, pulse shape, and pulse rate. Patient 6 may also select a program, e.g., from among a plurality of stored programs, as the present program to control delivery of stimulation by implantable stimulator 4.

In accordance with the techniques described in this disclosure, clinician programmer 20 and/or patient programmer 22 may be used to graphically define a desired stimulation field(s) within zones on or adjacent to one or more leads, and generate the stimulation parameters required to create a stimulation field represented by the zone or zones. In particular, clinician programmer 20 and/or patient programmer 22 may be used for translating one or more user input stimulation zones into a set of electrodes for delivering electrical stimulation therapy to a patient, determining the variable electrical stimulation contributions of each electrode to the zone, and determining amplitudes of electrical stimulation delivered by the individual electrodes when using zone-based programming. Clinician programmer 20 and/or patient programmer 22 may also be used for graphically representing the stimulation zone and receiving input from a user that manipulates the shape and position of the zone. In response to such manipulation of shape and/or position, the programmer may automatically adjust stimulation amplitude contributions of the electrodes that deliver stimulation defining the zone. For example, the total current may be redistributed between electrodes in a zone as the zone shape changes such that the total current is maintained equally throughout the zone. In some examples, the total current may be determined by the contributions of all electrodes in a zone and the total current may be scaled up or down according to the total contribution of all the electrodes.

In some examples, implantable stimulator 4 delivers stimulation according to a group of programs at a given time. Each program of such a program group may include respective values for each of a plurality of therapy parameters, such as respective values for each of current or voltage amplitude, pulse width, pulse shape, pulse rate and electrode configuration (e.g., electrode combination and polarity). Implantable stimulator 4 may interleave pulses or other signals according to the different programs of a program group, e.g., cycle through the programs, to simultaneously treat different symptoms or different body regions, or provide a combined therapeutic effect. In such examples, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by implantable stimulator 4.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art. Clinician programmer 20 and patient programmer 22 also may communicate with each other using any of a variety of local wireless communication techniques, such as RF communication according to the 802.11 or Bluetooth specification sets, infrared communication, e.g., according to the IrDA standard, or other standard or proprietary telemetry protocols. Each of clinician programmer 20 and patient programmer 22 may include a transceiver to permit bi-directional communication with implantable stimulator 4.

Generally, system 2 delivers stimulation therapy to patient 6 in the form of controlled current or voltage waveforms or controlled current or voltage pulses. The shapes of the pulses may vary according to different design objectives, and may include ramped or trapezoidal pulses, sinusoidal or otherwise curved pulses, stepped pulses having 2 or more discrete amplitudes, closely spaced pairs of pulses, and biphasic (positive and negative aspects within a single pulse) or monophasic (only positive or only negative aspects within a single pulse) variations of any of the above. In the case of current-based stimulation, implantable stimulator 4 regulates current that is sourced or sunk by one or more electrodes, referred to as regulated electrodes. In some examples, one of the electrodes may be unregulated. In such configurations, either the housing electrode or a lead electrode may be the unregulated electrode.

A source current may refer to a positive current that flows out of an electrode, e.g., from a regulated current source via a regulated current path to surrounding tissue, or from a reference voltage via an unregulated current path. Source currents may be depicted with a "+" sign. A sink current may refer to a negative current that flows into an electrode, e.g. from surrounding tissue and is sunk by a regulated current sink via a regulated current path or by a reference voltage via an unregulated current path. Sink currents may be depicted with a "−" sign. Regulated source currents may sum to produce a greater overall source current. Regulated sink currents may sum to produce a greater overall sink current. Regulated source and regulated sink currents may partially or entirely cancel one another, producing a net difference in the form of a net source current or sink current in the case of partial cancellation. In some examples, an unregulated current path can source or sink current approximately equal to this net difference. In other examples, regulated source and sink currents may be substantially balanced.

As mentioned above, in some example implementations, e.g., an omnipolar arrangement, one or more electrodes 11 may transfer stimulation pulses from the lead 10 to the tissue substantially simultaneously with stimulation pulses delivered via housing electrode 13. For example, housing electrode 13 and one or more electrodes 11 may be configured to act as anodes and source current. Substantially simultaneously delivering stimulation via both a housing anode and one or more lead anodes may allow a user to achieve different electric field shapes by controlling current paths between the housing anode and the lead anode(s) in a relative manner. In other example implementations, e.g., a bipolar/multipolar arrangement, one or more electrodes 11 may be configured to act as anodes and source current while one or more different electrodes 11 may be configured to act as cathodes and sink current. In another example implementation, e.g., a unipolar arrangement, housing electrode 13 may be configured to act as an anode and source current while one or more electrodes 11 on one or more leads are configured to act as cathodes and sink current. Techniques of this disclosure may be implemented using unipolar arrangements, bipolar/multipolar arrangements, and omnipolar arrangements.

Figure 2:
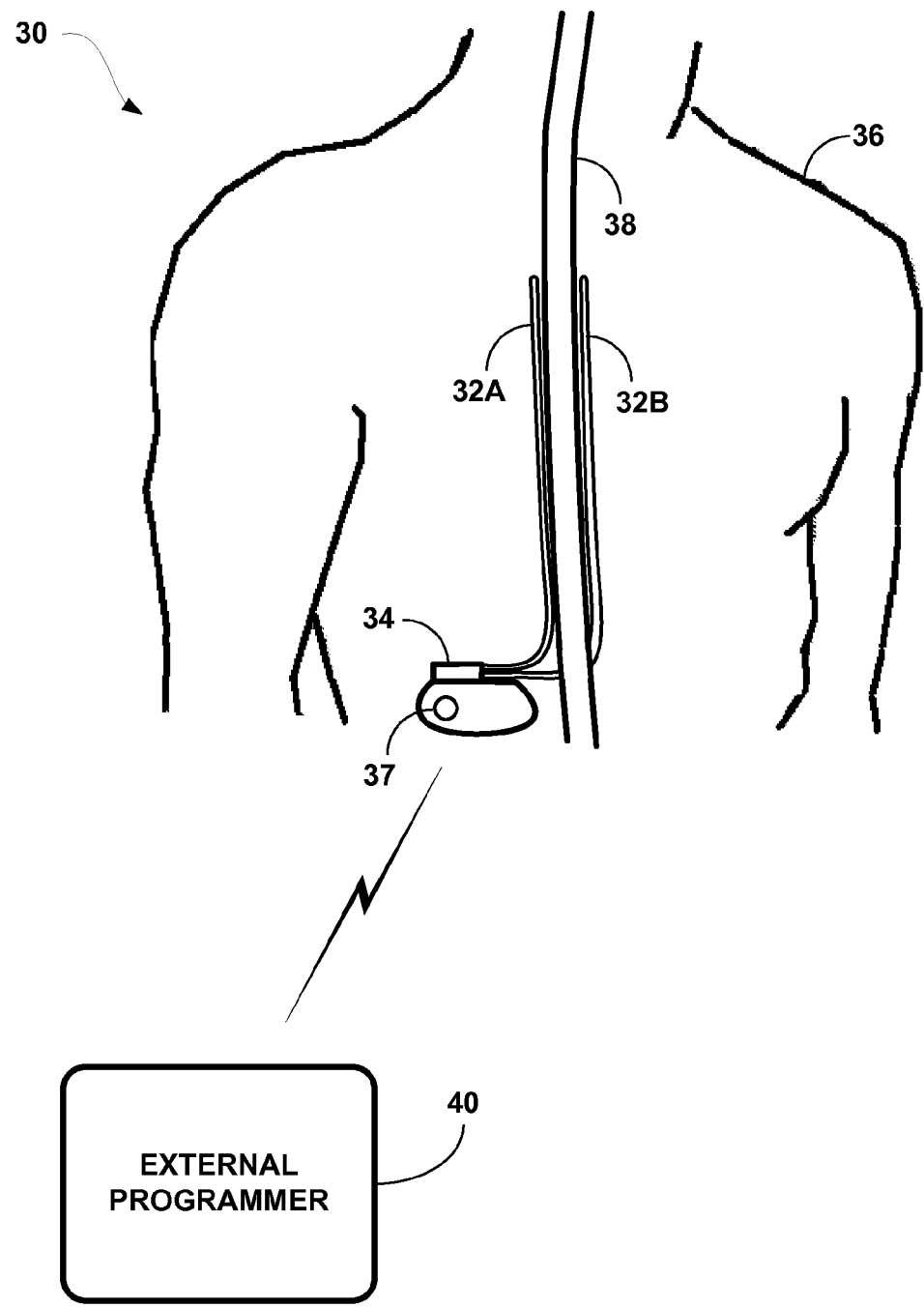
FIG. 2 is a conceptual diagram illustrating another example therapy system that includes an implantable stimulator coupled to a stimulation lead.

FIG. 2 is a conceptual diagram illustrating system 30 that delivers stimulation therapy to spinal cord 38 of patient 36. Other electrical stimulation systems may be configured to deliver electrical stimulation to gastrointestinal organs, pelvic nerves or muscle, peripheral nerves, or other stimulation sites. In the example of FIG. 2, system 30 delivers stimulation therapy from implantable stimulator 34 to spinal cord 38 via one or more electrodes (not shown) carried by, i.e., located on, implantable medical leads 32A and 32B (collectively "leads 32") as well as the housing of implantable stimulator 34, e.g., housing electrode 37. System 30 and, more particularly, implantable stimulator 34 may operate in a manner similar to implantable stimulator 4 (FIG. 1). That is, in a current-based example, implantable stimulator 34 delivers controlled current stimulation pulses or waveforms to patient 36 via one or more regulated, stimulation electrodes. Alternatively, implantable stimulator 34 may be configured to deliver controlled voltage pulses. As additional control means, the implantable stimulator 34 may be configured to deliver constant power pulses or pulses with a controlled amount of total charge movement in Coulombs. As mentioned above, in some examples, one of the electrodes may be unregulated.

In the example of FIG. 2, the distal ends of leads 32 carry electrodes that are placed adjacent to the target tissue of spinal cord 38. The proximal ends of leads 32 may be both electrically and mechanically coupled to implantable stimulator 4 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing. Application of certain techniques will be described in this disclosure with respect to implantable stimulator 34 and implantable leads 32 having ring electrodes for purposes of illustration. However, other types of electrodes may be used.

Stimulator 34 may be implanted in patient 36 at a location minimally noticeable to the patient. For SCS, stimulator 34 may be located in the lower abdomen, lower back, or other location to secure the stimulator. Leads 32 are tunneled from stimulator 34 through tissue to reach the target tissue adjacent to spinal cord 38 for stimulation delivery. In an omnipolar arrangement, for example, at the distal ends of leads 32 are one or more electrodes (not shown) that transfer the stimulation pulses from the lead to the tissue substantially simultaneously with stimulation pulses delivered via a housing electrode, e.g., electrode 37. Some of the electrodes may be electrode pads on a paddle lead, circular (i.e., ring) electrodes surrounding the body of leads 32, conformable electrodes, cuff electrodes, segmented electrodes, or any other type of electrodes capable of forming unipolar, bipolar or multi-polar electrode configurations.

As used in one example implementation of the techniques of this disclosure, e.g., an omnipolar arrangement, substantially simultaneous delivery of stimulation, whether current or voltage or power or charge, refers to the partial or complete time-wise synchronization of the electrical stimulation pulses or waveforms. Complete time-wise synchronization may refer to the housing electrode, e.g., anode, delivering stimulation at the same time that one or more lead electrodes, e.g., anodes, deliver stimulation. For example, complete time-wise synchronization may include the rising edge of the stimulation pulse or waveform being delivered by the housing electrode, e.g., anode, substantially coinciding with the rising edge of the stimulation pulse or waveform being delivered by the one or more lead electrodes, e.g., anodes, and the falling edge of the stimulation pulse or waveform being delivered by the housing electrode, e.g., anode, coinciding with the falling edge of the stimulation pulse or waveform being delivered by the one or more lead electrodes, e.g., anodes. Complete time-wise synchronization may also include a pulse delivered by a housing anode, for example, being delivered within the pulse width of a pulse delivered by a lead anode, for example. Partial time-wise synchronization may refer to the housing electrode, e.g., anode, delivering one electrical stimulation pulse or waveform while at least one lead electrode, e.g., anode, is delivering another electrical stimulation pulse or waveform such that at least a portion of one of the rising or falling edge of one pulse or waveform overlaps in time with at least a portion of one of the rising or falling edge of at least one other pulse or waveform.

Implantable stimulator 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. The stimulation delivered by implantable stimulator 34 may take the form of stimulation pulses or continuous stimulation waveforms, and may be characterized by controlled current or voltage levels, as well as programmed pulse widths and pulse rates in the case of stimulation current pulses. Stimulation may be delivered via selected combinations of electrodes located on one or both of leads 32 and on the housing. Stimulation of spinal cord 38 may, for example, prevent pain signals from traveling through the spinal cord and to the brain of the patient. Patient 34 perceives the interruption of pain signals as a reduction in pain and, therefore, efficacious therapy.

With reference to FIG. 2, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry.

In accordance with certain techniques described in this disclosure, programming of stimulator 34 may also include graphically defining a desired stimulation field(s) within zones on or adjacent to one or more leads, and generating, via a programmer, the current stimulation required to create the stimulation field. Programming of stimulator 34 may also include translating one or more user input stimulation zones into a set of electrodes for delivering electrical stimulation therapy to a patient, determining the variable electrical stimulation contributions of each electrode to the zone, and determining amplitudes of electrical stimulation to be delivered by the individual electrodes when using zone-based programming, in accordance with this disclosure. Programming may further include manipulating the shape and position of the zone, including behaviors of the zone while moving and when colliding with other zones or violating system interlocks such as zone limits or boundaries or charge balance constraints.

An example interlock may be a stretch of a cathodal zone that requires more cathodal current than could be generated by the existing anodal zones (including the can). In this case, the system may block further stretches and prompt the user to add an anode to the configuration. Alternately, the system may automatically add an anode "far" away from the stretching cathode, e.g., on the other end of a lead, or at least several electrodes away. Or, in some implementations, a limit or threshold may be placed on a per electrode charge density. Such a limit may prevent the current output for an electrode of a given surface area. When the system reaches this limit, the system may prevent further current increases, for example. In other examples, the system may prompt the user with an indication that the limit has been reached before continuing with current increases.

In some cases, external programmer 40 may be characterized as a physician or clinician programmer, such as clinician programmer 20 (FIG. 1), if it is primarily intended for use by a physician or clinician. In other cases, external programmer 40 may be characterized as a patient programmer, such as patient programmer 22 (FIG. 1), if it is primarily intended for use by a patient. In general, a physician or clinician programmer may support selection and generation of programs by a clinician for use by stimulator 34, whereas a patient programmer may support adjustment and selection of such programs by a patient during ordinary use.

Whether programmer 40 is configured for clinician or patient use, programmer 40 may communicate to implantable stimulator 4 or any other computing device via wireless communication. Programmer 40, for example, may communicate via wireless communication with implantable stimulator 4 using radio frequency (RF) telemetry techniques known in the art. Programmer 40 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with implantable stimulator 4 and other programming devices via remote telemetry techniques known in the art, communicating via a local area network (LAN), wide area network (WAN), public switched telephone network (PSTN), or cellular telephone network, for example.

Figure 3:
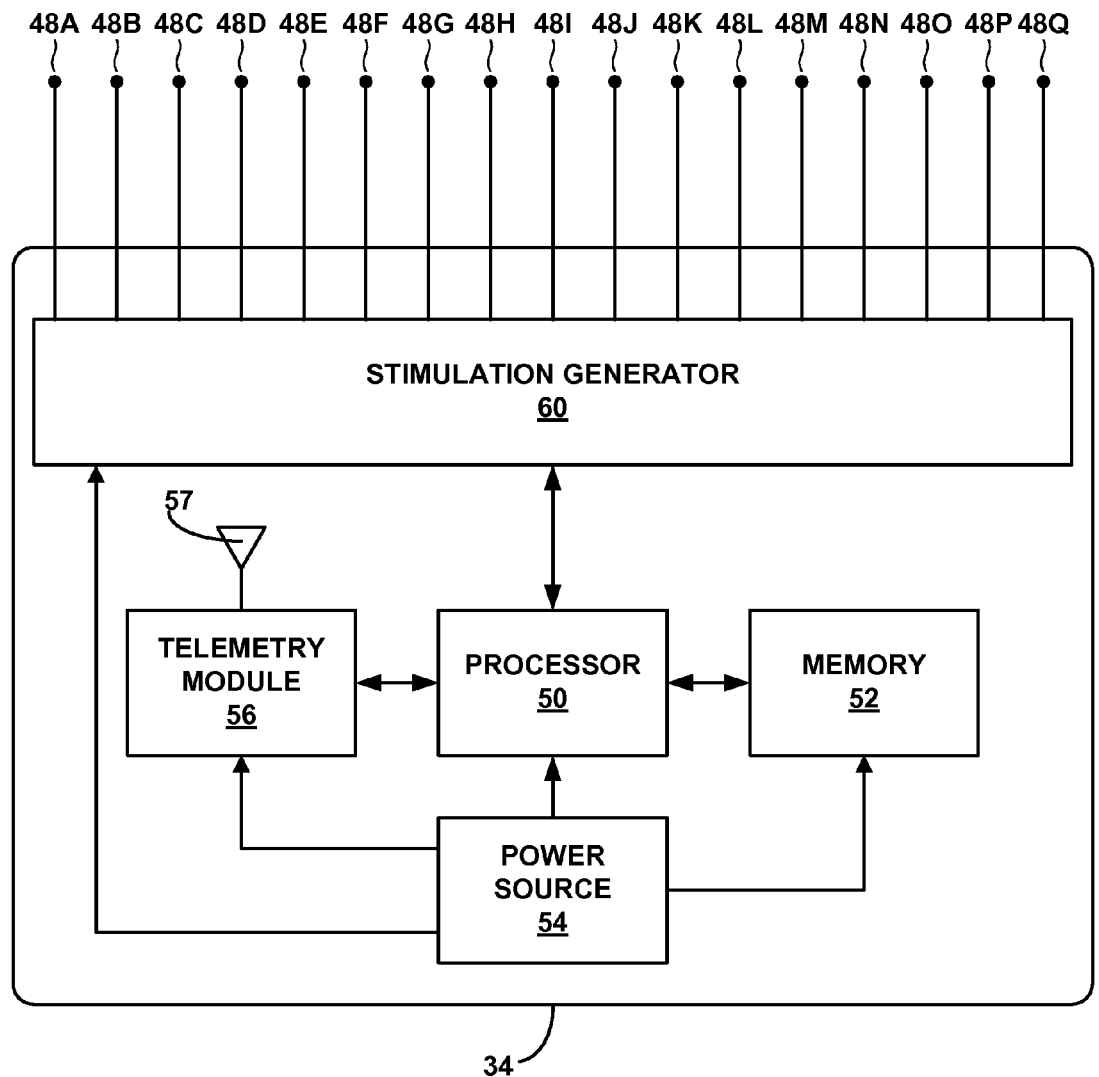
FIG. 3 is a block diagram illustrating various example components of an implantable electrical stimulator.

FIG. 3 is a block diagram illustrating various components of an example implantable stimulator 34. Although the components shown in FIG. 3 are described in reference to implantable stimulator 34, the components may also be included within implantable stimulator 4 shown in FIG. 1 and used within system 2. In the example of FIG. 3, implantable stimulator 34 includes processor 50, memory 52, power source 54, telemetry module 56, antenna 57, and a stimulation generator 60. Implantable stimulator 34 is also shown in FIG. 3 coupled to electrodes 48A-Q (collectively "electrodes 48"). Electrodes 48A-48P are implantable and may be deployed on one or more implantable leads. With respect to FIG. 1, lead segments 12A and 12B may carry electrodes 48A-H and electrodes 48I-P, respectively. In some cases, one or more additional electrodes may be located on or within the housing of implantable stimulator 34, e.g., to provide a common or ground electrode or a housing anode. With respect to FIG. 2, leads 32A and 32B may carry electrodes 48A-H and electrodes 48I-P, respectively. In the examples of FIGS. 1 and 2, a lead or lead segment carries eight electrodes to provide a 2×8 electrode configuration (two leads with 8 electrodes each), providing a total of sixteen different electrodes. The leads may be detachable from a housing associated with implantable stimulator 34, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), two or more leads with 11 or 13 electrodes, or other configurations. Different electrodes are selected to form electrode combinations. Polarities are assigned to the selected electrodes to form electrode configurations.

Electrode 48Q represents one or more electrodes that may be carried on a housing, i.e., can, of implantable stimulator 4. Electrode 48Q may also be a dedicated short lead extending from the housing, or a proximal portion of one of the leads carrying electrodes 48A-48P. The proximal portion may be closely adjacent to the housing, e.g., at or near a point at which a lead is coupled to the housing, such as adjacent to a lead connection header 8 of the housing. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of implantable stimulator 4, such as stimulation generator 60, processor 50, memory 52, telemetry module 56, and power source 54.

Housing electrode 48Q may be configured for use as an anode to source current substantially simultaneously with one or more electrodes 48A-48P configured for use as cathodes sinking current in a unipolar arrangement. Housing electrode 48Q may be configured for use as an anode to source current substantially simultaneously with current sourced by another electrode 48A-48P configured for use as an anode in an omnipolar arrangement. By way of specific example, electrodes 48A, 48B, and housing electrode 48Q each could be configured for use as anodes. Electrodes 48A, 48B could deliver electrical stimulation current substantially simultaneously with the electrical stimulation current delivered via housing electrode 48Q. In this illustration, one or more cathodes could be formed with other electrodes (e.g., any of electrodes 48C-48P) on the leads to sink current sourced by anodes 48A, 48B and 48Q.

Memory 52 may store instructions for execution by processor 50, stimulation therapy data, sensor data, and/or other information regarding therapy for patient 6. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 4, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with current amplitudes, pulse widths (if applicable), and rates specified by one or more stimulation programs. Processor 50 may also control stimulation generator 60 to selectively deliver the stimulation via subsets of electrodes 48, also referred to as electrode combinations, and with polarities specified by one or more programs.

Upon selection of a particular program group, processor 50 may control stimulation generator 60 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. The electrode combination may specify particular electrodes in a single array or multiple arrays, and on a single lead or among multiple leads. The electrode combination may include at least one anode on the housing of the IMD, e.g., electrode 48Q, at least one anode on a lead, electrode 48A, and at least one cathode on a lead. The lead-borne anode and cathode may be on the same lead or different leads, if more than one lead is provided. A program may be defined directly, by selecting parameters and electrodes, or by zone-based programming, in which parameters and electrodes are automatically determined by the programmer in response to manipulation or positioning of stimulation zones.

Stimulation generator 60 is electrically coupled to electrodes 48A-P via conductors of the respective lead, such as lead 12 in FIG. 1 or leads 32 in FIG. 2, in implementations in which electrodes 48A-P are carried by, located on, leads. Stimulation generator 60 may be electrically coupled to one or more housing ("can") electrodes 48Q via an electrical conductor disposed within the housing of implantable stimulator 4 (FIG. 1) or implantable stimulator 34 (FIG. 3). Housing electrode 48Q may be configured as a regulated or unregulated electrode to form an electrode configuration in conjunction with one or more of electrodes 48A-48P located on leads of the IMD. Housing electrode 48Q may be configured for use as an anode to source current substantially simultaneously with one or more electrodes, e.g., any of electrodes 48A-48P, on one or more leads configured for use as anodes.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50.

For example, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

In one example implementation, e.g., an omnipolar arrangement, stimulation generator 60 may be configured to deliver stimulation using one or more of electrodes 48A-P as stimulation electrodes, e.g., anodes, while substantially simultaneously delivering stimulation using housing electrode 48Q as a stimulation electrode, e.g., anode. The anodes on the lead(s) and the housing may be used to deliver stimulation in conjunction with one or more cathodes on the lead(s). As one illustration, an electrode combination selected for delivery of stimulation current may comprise an anode on the IMD housing, and anode on a lead, and a cathode on the same lead or a different lead. In other examples, the electrode combination may include multiple anodes and/or multiple cathodes on one or more leads in conjunction with at least one anode on the IMD housing. In some examples, the electrode combination may include one or more anodes on one or more leads, and one or more cathodes on the same lead or a different lead, e.g., a bipolar/multipolar arrangement. In other examples, the electrode combination may include an anode on the housing, and one or more cathodes on one or more leads, e.g., omnipolar arrangement. In yet another example, the electrode combination may include a cathode on the housing, and one or more additional cathodes on one or more leads, along with one or more anodes also on the leads, e.g., a variation of an omnipolar arrangement.

Telemetry module 56 may include a radio frequency (RF) transceiver to permit bi-directional communication between implantable stimulator 4 and each of clinician programmer 20 and patient programmer 22. Telemetry module 56 may include an antenna 57 that may take on a variety of forms. For example, antenna 57 may be formed by a conductive coil or wire embedded in a housing associated with medical device 4. Alternatively, antenna 57 may be mounted on a circuit board carrying other components of implantable stimulator 4 or take the form of a circuit trace on the circuit board. In this way, telemetry module 56 may permit communication with clinician programmer 20 and patient programmer 22 in FIG. 1 or external programmer 40 in FIG. 2, to receive, for example, new programs or program groups, or adjustments to programs or program groups.

Power source 54 may be a non-rechargeable primary cell battery or a rechargeable battery and may be coupled to power circuitry. However, the disclosure is not limited to embodiments in which the power source is a battery. In another embodiment, as an example, power source 54 may comprise a supercapacitor. In some embodiments, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional embodiments, power source 54 may include a small rechargeable circuit and a power generation circuit to produce the operating power. Recharging may be accomplished through proximal inductive interaction between an external charger and an inductive charging coil within stimulator 4. In some embodiments, power requirements may be small enough to allow stimulator 4 to utilize patient motion at least in part and implement a kinetic energy-scavenging device to trickle charge a rechargeable battery. A voltage regulator may generate one or more regulated voltages using the battery power.

Figure 4:
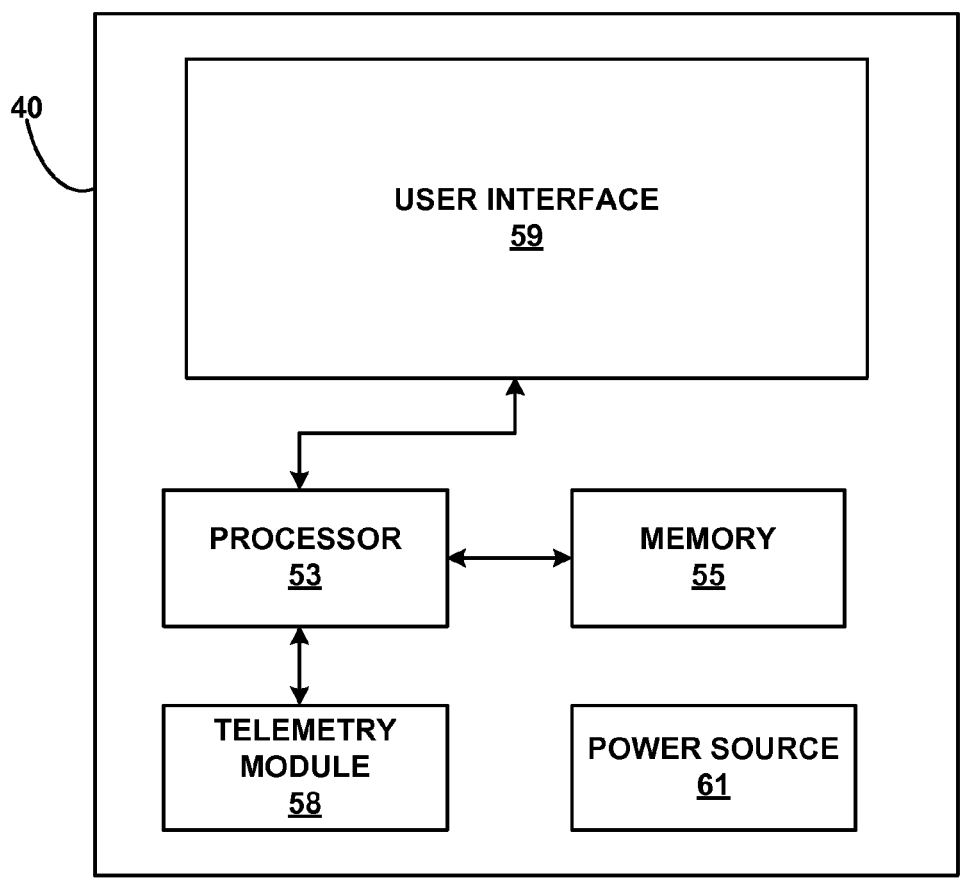
FIG. 4 is a block diagram illustrating various example components of an external programmer for use with an electrical stimulator.

FIG. 4 is a functional block diagram illustrating various components of an external programmer 40 for an implantable stimulator 14. Although the components shown in FIG. 4 are described in reference to external programmer 40, the components may also be included within clinician programmer 20 or patient programmer 22 shown in FIG. 1. As shown in FIG. 4, external programmer 40 includes processor 53, memory 55, telemetry module 58, user interface 59, and power source 61. In general, processor 53 controls user interface 59, stores and retrieves data to and from memory 55, and controls transmission of data with implantable stimulator 34 through telemetry module 58. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 40 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 4, such as therapy delivery values.

A clinician or patient 36 interacts with user interface 59 in order to, for example, manually select, change or modify programs, adjust voltage or current amplitude, provide efficacy feedback, or view stimulation data. User interface 59 may include a screen and one or more input buttons that allow external programmer 40 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

Using certain techniques of this disclosure, a clinician or patient 36 may graphically define a desired stimulation field(s) within zones on or adjacent to one or more leads using interface 59. In particular, user interface 59 may be used for graphically representing the stimulation zone and receiving input from a user that manipulates the shape and position of the zone, as will be described in more detail below.

Telemetry module 58 allows the transfer of data to and from stimulator 34. Telemetry module 58 may communicate automatically with stimulator 34 at a scheduled time or when the telemetry module detects the proximity of the stimulator. Alternatively, telemetry module 58 may communicate with stimulator 34 when signaled by a user through user interface 59. To support RF communication, telemetry module 44 may include appropriate electronic components, such as amplifiers, filters, mixers, encoders, decoders, and the like.

Programmer 40 may communicate wirelessly with implantable stimulator 34 using, for example, RF communication or proximal inductive interaction. This wireless communication is possible through the use of telemetry module 44 which may be coupled to an internal antenna or an external antenna. Telemetry module 44 may be similar to telemetry module 58 of implantable stimulator 34.

Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication, e.g., based on the IrDA standard.

Power source 46 delivers operating power to the components of programmer 40. Power source 46 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

Figure 5:
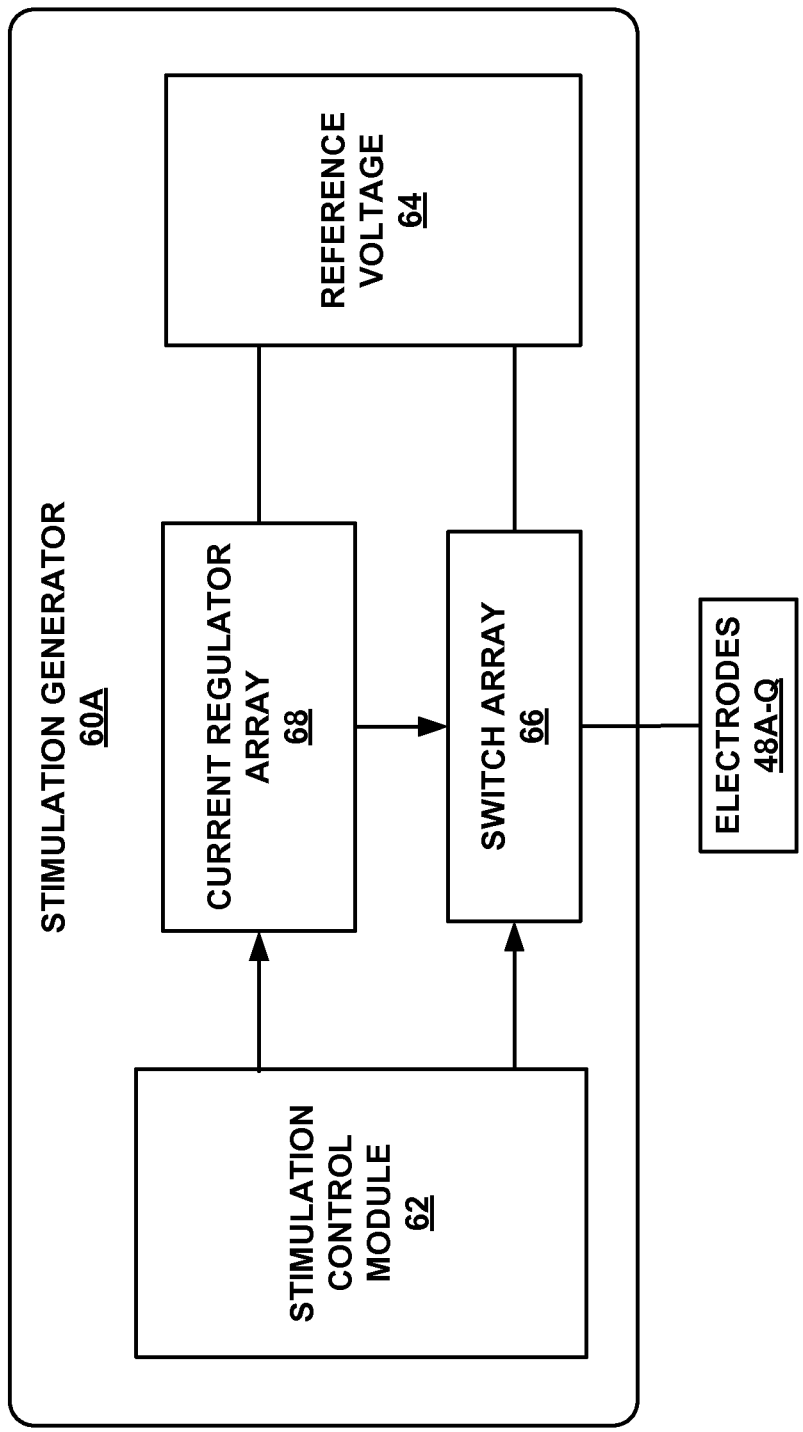
FIG. 5 is a block diagram illustrating various components of an example electrical stimulation generator for use in the implantable electrical stimulator of FIG. 3.

FIG. 5 is a block diagram illustrating various components of an example stimulation generator 60A. Stimulation generator 60A may be used with an implantable stimulator, e.g., to perform the functions of stimulation generator 60 as described with reference to FIGS. 1-3. Although described with respect to implantable stimulator 4, stimulation generator 60A may also be used for implantable stimulator 34, or other types of stimulators. In the example of FIG. 5, stimulation generator 60A is selectively, e.g., based on a signal from processor 50 (FIG. 3), configured to deliver controlled current stimulation pulses to patient 6 via various electrode combinations. However, the disclosure is not limited to examples in which regulated current pulses are delivered. In other examples, stimulation generator 60A may provide continuous, regulated current waveforms, rather than regulated current pulses. In still other examples, stimulation generator 60A may deliver combinations of continuous waveforms and pulses, or selectively deliver either continuous waveforms or pulses. Stimulation generator 60A may generate either controlled current-based or controlled voltage-based stimulation in the form of pulses or continuous waveforms. It may also be controlled to provide constant power (current-voltage product) or controlled charge stimulation pulses. Additionally, it may be configurable to deliver any of these variously controlled pulse amplitudes in a variety of pulse shapes (trapezoidal or ramped, sinusoidal or otherwise curved, or stepped).

In the example illustrated in FIG. 5, stimulation generator 60A includes stimulation control module 62, reference voltage source 64, switch array 66, and current regulator array 68. Reference voltage source 64 may provide operating power to current regulator array 68, and may include a regulated voltage that sets the level of the reference voltage. As shown in FIG. 5, reference voltage source 64 may be coupled to provide operating power for the current regulator array 68 and provide a reference voltage for connection to electrodes 48A-48Q for an unregulated mode of electrode operation. In other examples, however, the voltage level of the reference voltage and the operating voltage level provided to regulated current source array 68 may be different.

Stimulation control module 62 forms a stimulation controller that controls switch array 66 and current regulator array 68 to deliver stimulation via electrodes 48A-48Q. Stimulation control module 62 may include one or more microprocessors, microcontrollers, digital signal processors (DSPs), application-specific integrated circuits (ASICs), field-programmable gate arrays (FPGAs), or other integrated or discrete logic circuitry. In operation, stimulation control module 62 may control delivery of electrical stimulation according to one or more programs that may specify stimulation parameters such as electrode combination, electrode polarity, stimulation current amplitude, pulse rate, and/or pulse width as well as the percentage of source current distributed among or contributed by a housing anode and one or more lead anodes on one or more leads, and the percentage of sink current sunk by one or more cathodes. Programs may be defined by a user via an external controller and downloaded to an implantable stimulator 4 or 34 for use by stimulation control module 62.

Current regulator array 68 includes a plurality of regulated current sources or sinks Again, a current regulator may function as either a current source or sink, or be selectively configured to operate as either a source or a sink. For convenience, however, the term "current regulator" may be used in some instances to refer to either a source or sink. Hence, each of the current regulators in current regulator array 68 may operate as a regulated current source that delivers stimulation via a corresponding one of electrodes 48A-Q or a regulated current sink that receives current from a corresponding one of electrodes 48A-Q, where electrodes 48A-48Q may be provided on leads, on a stimulator housing, on a leadless stimulator, or in other arrangements. In general, electrodes 48A-48Q may be referred to below as electrodes 48 for conciseness.

Each switch of switch array 66 couples a corresponding one of electrodes 48 to either a corresponding bidirectional current regulator of current regulator array 68 or to reference voltage 64. In some examples, stimulation control module 62 selectively opens and closes switches in switch array 66 to configure a housing electrode, e.g., electrode 48Q, and one or more of electrodes 48A-48P on one or more leads as regulated electrodes by connection to regulated current sources or sinks in current regulator array 68. In other examples, stimulation control module 62 may selectively open and close switches in switch array 66 to configure either the housing electrode, e.g., electrode 48Q, or an electrode on the lead as an unregulated electrode by connection to reference voltage 64. In addition, stimulation control module 62 may selectively control individual regulated current sources or sinks in current regulator array 68 to deliver stimulation current pulses to the selected electrodes.

Reference voltage 64 may be a high or low voltage supplied by a regulated power source, depending on whether an electrode is programmed to be an unregulated source (high voltage rail) or unregulated sink (low voltage rail). Hence, reference voltage 64 may produce high and low reference voltages for selective coupling to unregulated, reference electrodes as needed given the selected electrode configuration. A regulated power source may produce one or more regulated voltage levels for use as reference voltage 64 and for use as a power rail for current regulator array 68. Again, although the same reference voltage 64 is coupled to current regulator array 68 in FIG. 5, different voltage levels could be used for the reference voltage coupled to switch array 66 and the operating voltage level provided to the regulated current source array. A regulated power source may generate the regulated voltages from voltages provided by a power source 54 (FIG. 3), such as a battery.

Stimulation control module 62 controls the operation of switch array 66 to produce electrode configurations defined by different stimulation programs. In some cases, the switches of switch array 66 may be metal-oxide-semiconductor field-effect-transistors (MOSFETs) or other circuit components used for switching electronic signals. The switches of switch array 66 may be designed to carry an amount of unregulated current that may be coupled to a corresponding electrode through an unregulated current path associated with reference voltage 64. As previously described, in some examples, two or more regulated, stimulation electrodes 48 may be intentionally programmed to deliver different amounts of current such that the regulated electrodes produce an unbalanced current distribution. In other examples, regulated source and sink current may be balanced such that substantially all current may be sourced and sunk via respective regulated current sources and sinks.

To provide individual control of electrodes 48 as either regulated electrodes or as unregulated, reference electrodes, stimulation control module 62 controls operation of switch array 66, and current regulator array 68. When stimulation is delivered to patient 6, for the example of current pulses, stimulation control module 62 controls switch array 66 to couple selected stimulation electrodes for a desired electrode combination to respective current regulators of current regulator array 68 or to reference voltage 64, as needed. Stimulation control module 62 controls the regulated bidirectional current sources of current regulator array 68 coupled to regulated electrodes to source or sink specified amounts of current. For example, stimulation control module 62 may control selected current sources or sinks on a pulse-by-pulse basis to deliver current pulses to corresponding electrodes.

Stimulation control module 62 also deactivates the regulated bidirectional current regulators of current regulator array 68 tied to inactive electrodes, i.e., electrodes that are not active as regulated electrodes in a given electrode configuration. Each regulated bidirectional current regulator of current regulator array 68 may include an internal enable switch controlled by stimulation control module 62 that disconnects regulated power source 64 from the current regulator or otherwise disables the current source when the corresponding electrode is not used as a regulated electrode to deliver stimulation.

In accordance with this disclosure, various techniques are described for translating one or more user input stimulation zones into a set of electrodes for delivering electrical stimulation therapy to a patient, determining the variable electrical stimulation contributions of each electrode to the zone, and determining amplitudes of electrical stimulation delivered via individual electrodes associated with a zone when using zone-based programming. In zone-based programming, a user may graphically define a desired stimulation field(s) within zones on or adjacent to one or more leads, and a programmer may generate the current stimulation required to create the stimulation field.

Several definitions are provided below:

An achievable stimulation region (ASR) is an on-screen region of a programmer display in which all stimulation must occur. The ASR is used for validity of placement and extent of stretching or moves of a stimulation zone by a user. Using various input media, a user may size (e.g., by stretching or contracting), shape, or move a zone. The ASR may be a convex hull enclosing all leads' electrodes. It may also be limited in extent by a distance threshold from an electrode, such that gaps between widely spaced leads are not shown to be part of the ASR and are thus not "achievable."

A stimulation zone is an area of stimulation defined by a collection of electrodes, their contributions, and an intensity. Stimulation zones may be cathodal, e.g., to indicate stimulation delivered via one or more cathodes in associated with the zone, or anodal, e.g., to indicate a guard/shield supported by one or more anodes associated with the zone. In operation, electrodes in anodal and cathodal zones may work together to define the overall electrical stimulation that is delivered via the lead or leads implanted in the patient. A display, e.g., of a programmer, may indicate a zone as being cathodal or anodal. Non-limiting examples by which zones may be indicated include colors, shades of gray (for black and white images), patterns (e.g., hatching patterns), and the like. As one non-limiting example, cathodal zones may be graphically represented by a first color, e.g., red, and anodal zones may be graphically represented by a second color, e.g., blue. The various zones may be represented by other colors, however, as well as different shading, patterns, and the like, as indicated above.

A field shape is a collection of one or more zones at a single time within a single program.

A zone shape, or indication of zone extent, is a graphical indication used to show which electrodes are recruited by a stimulation zone and their relative contributions to that zone. This may be a generally polygonal form, a set of curved boundaries formed by spline or Bezier curves, or a more complex shape calculated by finding the extent of the electromagnetic fields generated by a given combination of stimulation settings greater than a set threshold.

Recruited electrodes are those electrodes that are part of a given zone.

The electrode contribution is the degree to which a given electrode delivers its zone's desired intensity. The electrode contribution may have a value between 0.0 and 1.0.

Figure 6:
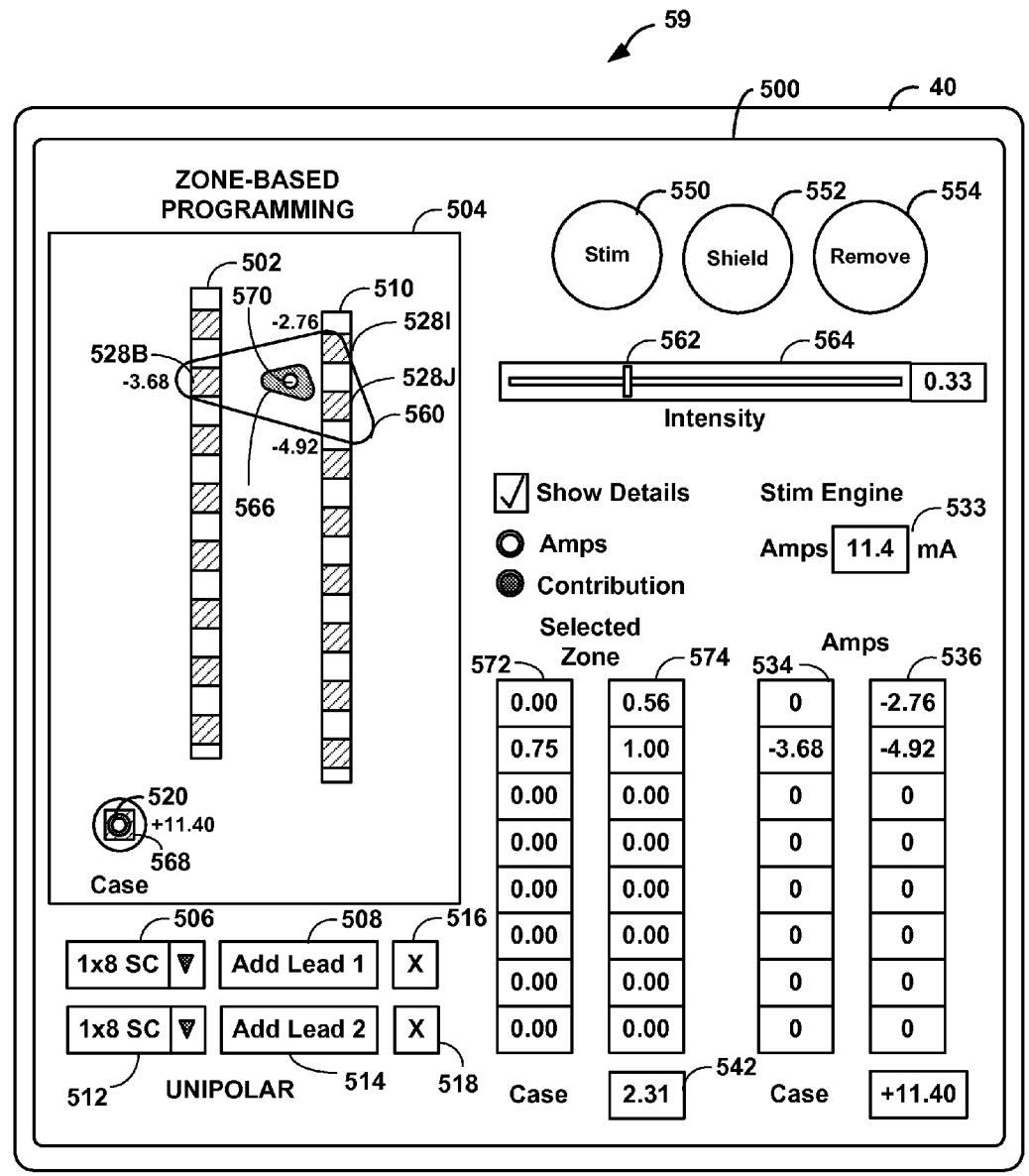
FIG. 6 is a schematic diagram illustrating an example user interface presented by the programmer of FIG. 4.

FIG. 6 depicts a user interface illustrating a unipolar stimulation arrangement created using zone-based programming. In zone-based programming, a user may graphically define a desired stimulation field(s) within zones on or adjacent to one or more leads, and processor 53 of programmer 40 may generate the current stimulation required to create the stimulation field.

FIG. 6 depicts user interface 59 provided by programmer 40. User interface 59 includes stimulation icon 550, shield icon 552, and removal icon 554 that may be used to create a desired stimulation field(s), as will be described in more detail below. User interface 59 includes display screen 500. Display screen 500 may be a touchscreen such that a stylus or other pointing media may be used to make selections directly on screen 500. Alternatively, or in addition, keys, buttons, wheels and other input devices may be provided on programmer 40, independently of display 500.

First lead 502 may be added to window 504 by first selecting a desired type of lead from pull-down menu 506 and then selecting "Add Lead 1" via icon 508. Similarly, second lead 510 may be added to window 504 by selecting the type of lead from pull-down menu 512 and then selecting "Add Lead 2" via icon 514. Leads may be added to window 504 by using a stylus, for example, and touching a location in the window for placement of the leads. In addition, the user may drag the leads placed in window 504 to a desired location. Icons 516, 518 allow a user to remove a lead from window 504. The housing electrode, or "case" electrode, indicated at 520 may, in some examples, be permanently displayed in window 504 for use with unipolar or omnipolar electrode arrangements. Other interface designs may place the lead configuration controls on separate screens.

In FIG. 6, user interface 59 is shown displaying a graphical representation of a stimulation zone, namely stimulation zone 560. In order to create zone 560, as in FIG. 6, a user may use a stylus, for example, and touch stimulation ("Stim") icon 550. The user may then use the stylus and touch a location, or zone, within window 504. For example, the user may touch an electrode on one of leads 502, 510, or a location near one of the electrodes or leads, e.g., between electrodes and leads. Touching an electrode with the stylus places a stimulation zone on the selected zone, e.g., the lead at the electrode. Touching an area or zone between a lead or an electrode places a stimulation zone on the selected zone, i.e., between the lead or electrode. Individual electrode values may be determined by their relative proximity to the location of the placed zone such that the nearest electrode is a full contributor (1.0) and others are scaled proportionally. In other examples, the user may be allowed to touch a desired location in the stimulation region, without resort to a first touch on an icon; subsequent touches in this example may cycle through zone options (e.g., stimulation, shield, off). The user may graphically manipulate, e.g., shape, move, shrink, and expand, the graphical representation of the stimulation zone by dragging, for example, the stimulation zone via the stylus to other areas, or zones, in window 504, e.g., electrodes or areas adjacent to electrodes, in order to create the desired shape of stimulation zone 560. Touching removal icon 554 with a stylus will remove the stimulation zone. In alternate designs, the stimulation zone may show specific control points to facilitate interaction. These may include an exaggerated border for stretching, a control at the centroid of the shape for moving, or specific boxes or dots at the corners to allow resizing.

The user may then use a stylus to move indicator 562 along horizontal scroll bar 564 to select the desired electrode intensity. In FIG. 6, the Selected Zone Intensity is 0.33, which is used to scale the electrode contributions of electrodes automatically selected to create stimulation zone 560 by the desired intensity to generate stimulation current amplitudes. Moving indicator 562 may modify all of the electrodes associated with a placed field or zone together. In addition, the intensity of the stimulation zone is graphically depicted at 566. The Selected Zone Intensity of 0.33 equates in this example to 11.4 mA of overall current stimulation, as indicated in current window 533, although intensity could also be communicated to the user in unitless quantities such as percentage of maximum or a fixed scale (0 to 10, 0 to 100, etc.). As indicator 562 of horizontal scroll bar 564 is moved to the right, the intensity is increased, depicted graphically at 566 and as indicator 562 of horizontal scroll bar 564 is moved to the left, the intensity is decreased. The intensity of case electrode 520 is graphically illustrated at 568. In some examples, intensity may be shown graphically as small areas of stimulation over each recruited electrode (proportional to their contributions) that grow until they merge at sufficient intensity levels. As mentioned above, case electrode 520 may be used in some example implementations, e.g., unipolar arrangements and omnipolar arrangements, and not other implementations, e.g., bipolar/multipolar arrangements. Upon selecting the desired electrode intensity, processor 53 of programmer 40 generates and depicts the current amplitudes associated with the desired zone 560, as seen in window 504. In another example, the user may specify whether case electrode 520 is an anode or cathode by selecting either the shield or sink icon, respectively, dragging the zone, and then setting the intensity via horizontal scroll bar 564. If a single stimulation zone has been selected by the user, changes to intensity may apply only to that selected zone. If no zones are selected, the intensity control may be disabled. Alternately, if no zones are selected, changes to intensity may scale all zones simultaneously by a fixed amount or a percentage of their current value.

A user may shape the stimulation zone by dragging, for example, the boundaries of the graphical representation of the stimulation zone displayed on the user interface via the stylus to other areas in window 504. For example, the user may click on a border, i.e., an outer perimeter, or an area near the border, of the stimulation zone, and drag it inward or outward to resize the stimulation zone. When a user clicks on the stimulation zone border and drags it, the stimulation zone may, for example, expand in the direction in which the user drags the stimulation zone.

In addition to shaping the stimulation zone by dragging, for example, the stimulation zone boundaries via the stylus to other areas in window 504, the center of stimulation zone 560 may be moved by dragging, for example, icon 570 representing the intensity of the stimulation zone. Dragging center icon 570 of stimulation zone 560 may result in the entire stimulation zone moving in the direction in which the user drags the stimulation zone. Dragging the stimulation zone may result in adjustments to the currents sunk (or sourced) by the electrodes producing stimulation 560.

In zone-based programming, the system may automatically determine the contributions of the three electrodes on the lead, 0.56, 0.75, and 1.00, shown in arrays 572, 574, which depict each of the zones on each of the two leads. Individual electrode values may be determined by their relative proximity to the location of the placed zone such that the nearest electrode is a full contributor (1.0) and others are scaled proportionally. The system, without manual intervention, then automatically scales the contributions by the desired intensity to generate stimulation current amplitudes to be delivered by the recruited electrodes. The system then defaults to a unipolar mode, and activates case electrode 520 to balance the sum of the three electrodes activated (4.92 mA+3.68 mA+2.76 mA=11.35 mA, with a small rounding error). The system may allow the user to choose whether to allow the case to be the default as a configurable option. If the case is allowed, it may further be selected to be used preferentially (such that the system uses it first until it reaches an interlock) or to be used equally (such that the system spreads anodal current around all active anodes in a balanced fashion). Using the case by default may be advantageous because it may require fewer user actions, e.g., the system automatically configured the case electrode, and may eliminate the need for user interactions on subsequent intensity changes, e.g., the user does not have to balance stimulation in order for the system to enter a valid, programmable state. The system may also default to the most energy efficient mode such that losses in the lead array are only applied once, because the return path does not traverse the lead array wires a second time.

As shown in FIG. 6, in a unipolar arrangement, case electrode 520 sources the desired 11.4 mA of current while electrodes 528I, 528B, 528J sink 2.76 mA, 3.68 mA, and 4.92 mA, respectively. The currents needed to generate zone 560 are shown in window 504 as well as in arrays 534, 536, which depict each of the electrodes on each of the two leads and the current in milliamps associated with the electrodes within the zones originally selected by the user. In addition, arrays 572, 574 indicate the contributions of the electrodes in the zone(s) originally selected by the user. In the example depicted in FIG. 6, the electrode that sinks (or sources, in other examples) the most current to produce a given zone has a first contribution of 1.0, and the contributions of the remaining zones used to produce that particular zone are a percentage of that first contribution. In FIG. 6, electrode 528J sinks 4.92 mA, a value greater than the currents sunk by electrodes 528B, 528I. As such, electrode 528J has a contribution of 1.0, and electrodes 528B, 528I have a contribution, respectively, of 3.68 mA/4.92 mA or about 0.75 and 2.76 mA/4.92 mA or about 0.56, as indicated in arrays 572, 574. In a unipolar arrangement, like in FIG. 6, case electrode 568 must source all of the desired current and, as such, it has a contribution of 1.0+0.75+0.56=2.31, as indicated at 542.

Figure 7A:
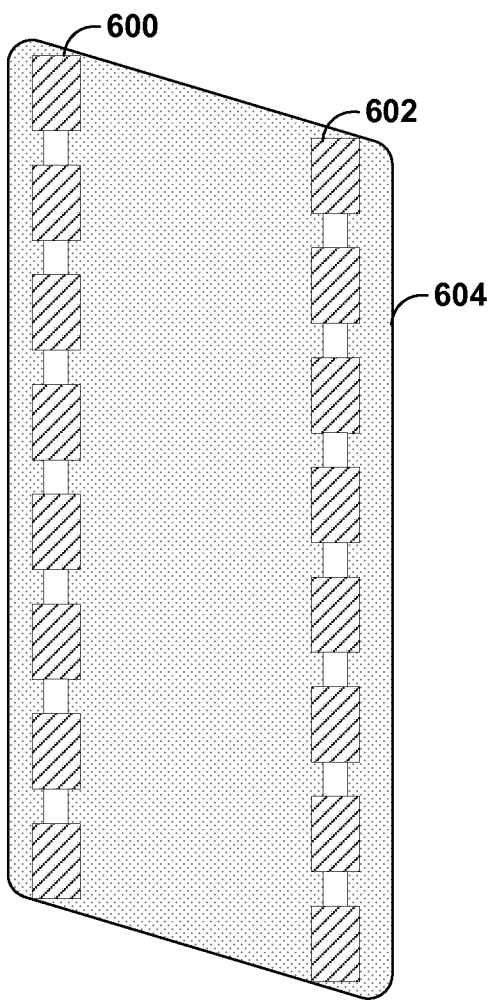
FIGS. 7A-7C are schematic diagrams depicting example achievable stimulation regions for various lead configurations.
Figure 7B:
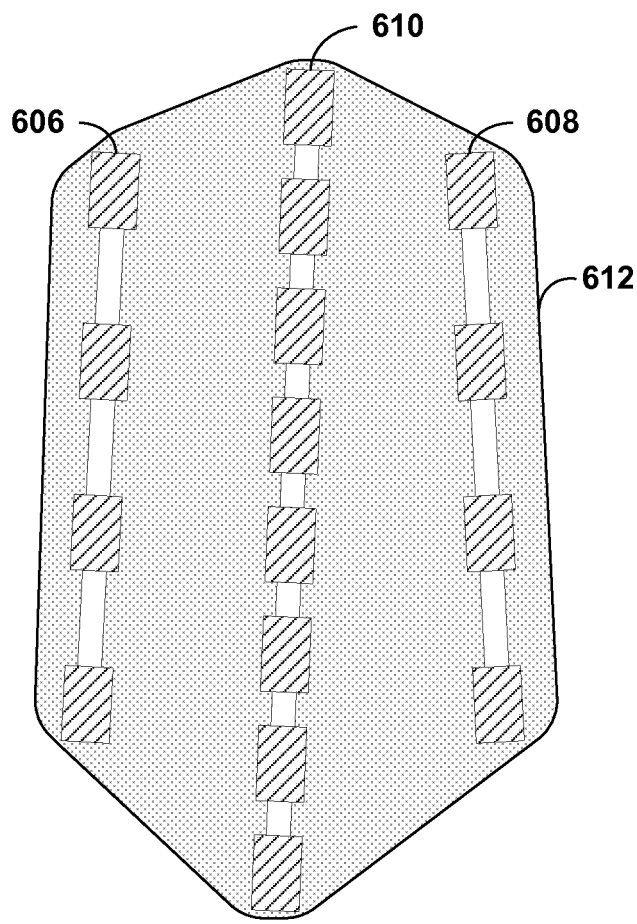
Figure 7C:
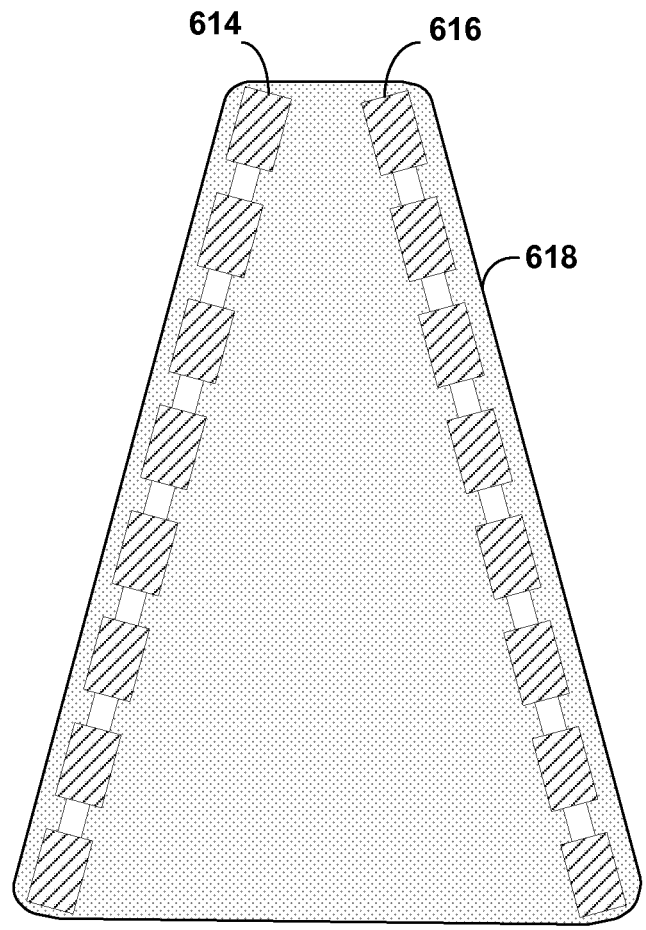

FIGS. 7A-7C are schematic diagrams depicting example achievable stimulation regions (ASRs) for various lead configurations. FIG. 7A depicts a 2×8 electrode configuration (two leads with 8 electrodes each), providing a total of sixteen different electrodes, surrounded by an ASR. Specifically, FIG. 7A depicts leads 600, 602 surrounded by ASR 604. FIG. 7B depicts a 2×4 electrode configuration in combination with a 1×8 configuration (two leads with 4 electrodes each combined with a one lead with 8 electrodes), providing a total of sixteen different electrodes, surrounded by an ASR. Specifically, FIG. 7B depicts leads 606, 608 (the 2×4 electrode combination) and lead 610 (the 1×8 configuration) surrounded by ASR 612. Like FIG. 7A, FIG. 7C depicts a 2×8 electrode configuration (two leads with 8 electrodes each), providing a total of sixteen different electrodes, surrounded by an ASR. Specifically, FIG. 7C depicts leads 614, 616 surrounded by ASR 618. However, unlike either FIG. 7A or FIG. 7B, the leads 614, 616 in FIG. 7C are not substantially parallel with one another. As seen in FIG. 7C, in some examples, ASR 618 may not indent, e.g., at the bottom of FIG. 7C where the two leads are spaced further apart then at the top.

Also, in some examples, an ASR may not have gaps for wide spaced leads. In one example, an ASR may be drawn by placing a ring of points, e.g., about twelve points, centered on the most distal and most proximal electrode of each lead of radius equal to 0.4 times the default size of a zone, thereby creating a convex hull around the points (which culls interior points). A polygon or other shape is then created from the remaining points. The ASR may specify the maximum outer spacing of the electrodes and/or leads from each other. In other examples, an ASR may be adjusted in cases where leads are deemed too far apart to allow stimulation to be achieved between them. This may be applied as a fixed threshold, a user determined distance, or a distance dynamically calculated based upon the lead geometries and the targeted anatomy. In such cases, a second region may be calculated based on these distance constraints and subtracted from the normally displayed ASR, thus yielding concave or otherwise irregular shapes.

As shown and described above with respect to FIG. 6, a user may graphically define a stimulation field(s) via zone-based programming. A user may select either a stimulation zone or a shield/guard zone for placement on the display, e.g., display screen 500, by selecting the stimulation icon 550 or shield icon 552, respectively, depicted in FIG. 6. In some examples, stimulation icon 550 and shield icon 552 may be colored, e.g., red and blue, respectively. After selecting either a stimulation zone or a guard zone for placement, the user may place the zone anywhere within the ASR, e.g., on a lead and between an electrode, directly on an electrode, between leads, and adjacent a single lead. During placement of the stimulation and/or guard zone, if the ASR is not already shown or if it is shown in the background, the user may receive a transient or emphasized (via animation, changes in opacity, changes in color, high contrast outlines, or other means) indication of the achievable stimulation region (ASR) to guide valid placement.

After a zone has been placed on the display screen, programmer 40 and, in particular, processor 53 defines, or "recruits," a set of electrodes, e.g., up to four electrodes, to generate the zone, without user intervention. In some examples, one or more electrodes may be recruited, i.e., selected by the programmer, based on their relative distance from the placed zone and such that their contributions are greater than a minimum threshold. The electrodes recruited by a zone may have independent contributions to the shape of the zone between 0 and 1.0, dependent on the relative distance from the electrode to the zone center. Electrode contributions may be scaled on a per zone basis such that the highest contributing electrode(s) are 1.0 and all others are less than or equal to 1.0.

In another example, electrodes may be recruited based on normalized distances. Programmer 40 and, in particular, processor 53 determines a distance between the zone placement point and each electrode on each lead. Processor 53 normalizes the determined distances, e.g., using the shortest determined distance between the zone placement point and an electrode. In order to determine the one or more electrodes that should be recruited to produce the desired stimulation zone, the normalized distances may be compared to a threshold value. By way of specific example, if the normalized distance between an electrode that is not already part of a stimulation region and the zone placement point is less than a threshold value of 1.4, then processor 53 may recruit the electrode. In other example implementations, the threshold value may be higher, or lower, than 1.4. The number of electrodes recruited by processor 53, which may be one electrode or more than four electrodes, depends on the lead configuration and the lead orientation. Individual contributions of recruited electrodes can be set to 1.0 for all electrodes or may be based on the normalized distance measurement on a per-electrode basis.

In some examples, the scaling of current amplitude contributions of electrodes may be accomplished by finding the distance between the selected zone placement point and all electrode centers of leads in the lead placement region. The scaling may be accomplished using actual current levels or the scaling may be unitless, e.g., percentages. The four shortest distances that do not cause a lead to be crossed with another lead (i.e., that do not cause electrodes to be recruited on a lead that is on the far side of a nearer lead from the point of placement) are then selected for recruitment. Contributions of recruited electrodes to the defined stimulation zone are determined, without user intervention, by finding the distance from the point to the recruited electrodes as a ratio of the total distance between electrodes separately in the x and y dimensions.

Figure 8A:
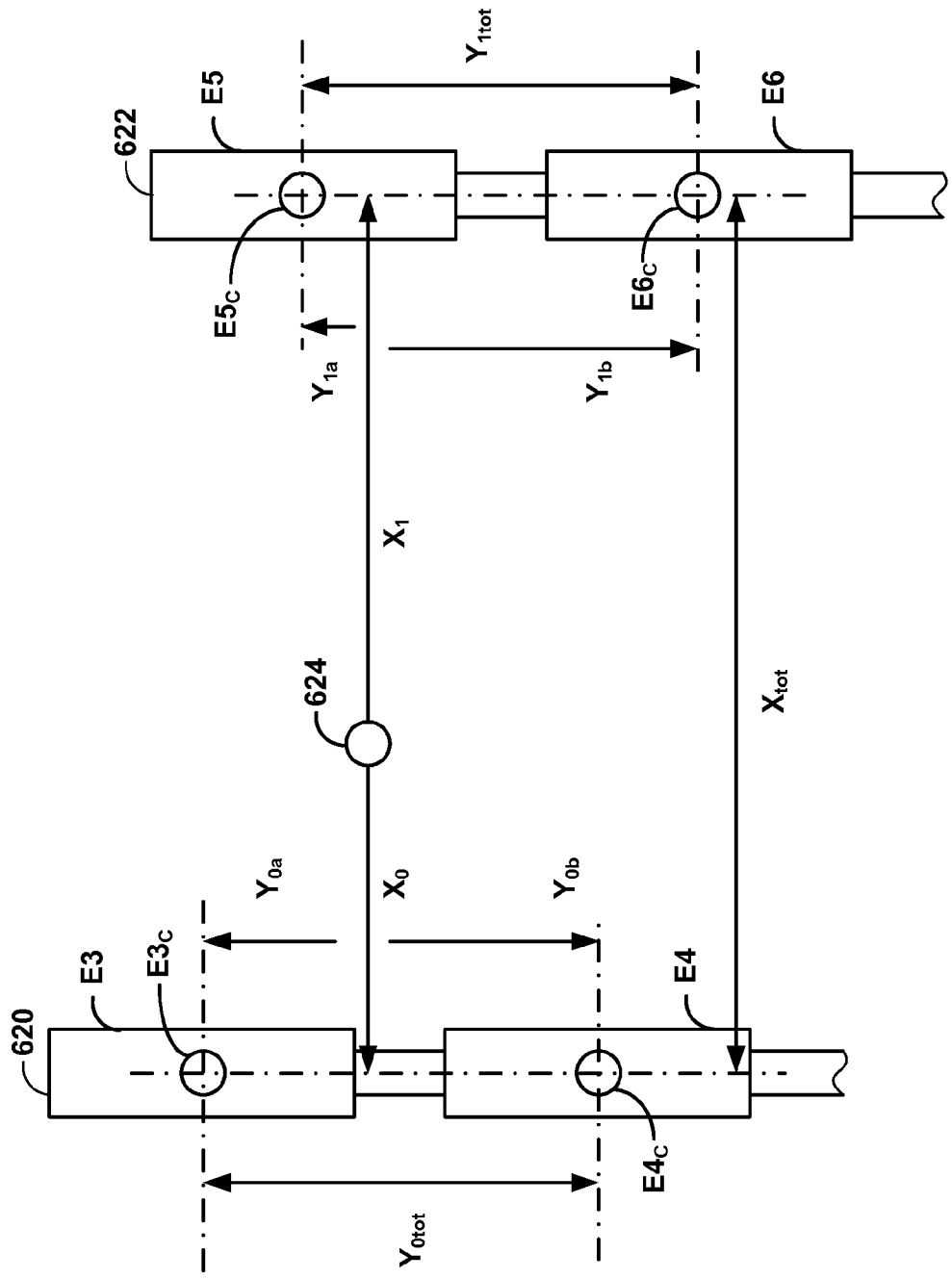
FIG. 8A is a schematic diagram illustrating an example electrode contribution determination using the techniques of this disclosure.

FIG. 8A is a schematic diagram illustrating an example electrode contribution determination using the techniques of this disclosure. In FIG. 8A, the contributions of electrodes E3 and E4 on lead 620 (the left lead) and electrodes E5 and E6 on lead 622 (the right lead) are determined by finding the distance from the selected zone placement point, shown at 624, as a ratio of the total distance between the electrodes, separately in the x and y dimensions. For lead 620, the electrode contributions, which may map proportionally to current amplitude contributions, are determined as follows:

$$E3 = (X_1/X_{tot})*(Y_{0b}/(Y_{0tot})$$

$$E4 = (X_1/X_{tot})*(Y_{0a}/(Y_{0tot})$$

And, for lead 622, the electrode contributions are determined as follows:

$$E5 = (X_0/X_{tot})*(Y_{1b}/Y_{1tot})$$

$$E6 = (X_0/X_{tot})*(Y_{1a}/Y_{1tot})$$

In some examples, the algorithm used to determine the electrode contributions may use an average of coordinates to find the single $X_0$ and $X_1$ values. Such an algorithm may be particularly useful when the leads are substantially vertical. In other examples, the algorithm may use the actual distances between the selected zone placement point and each electrodes' x-coordinate. It should be noted that because the electrode contributions are determined by ratios, the units of the distances may be in pixels, millimeters, or other units of measurement.

After the electrode contributions are determined for the recruited electrodes, the contributions may then be "thresholded," i.e., compared to a threshold value. Thresholding may prevent low electrode contributions values from being used to deliver stimulation, thus making the configuration more energy efficient. That is, if an electrode contribution is determined to be below a threshold value, e.g., below a value that would have any perceptible or therapeutic effect on the patient, the electrode may be turned off so that energy is not wasted. In some examples, thresholding may be accomplished by checking, for each of the recruited electrodes on a lead, e.g., two electrodes on a lead, if the contribution of one electrode is below a threshold value while the contribution of the other electrode on the lead is above the threshold value. If this is found, the contribution of the electrode that was below the threshold value is added to the contribution of the electrode that was above the threshold value and then the first electrode contribution, i.e., the electrode with the contribution below the threshold value, is zeroed, i.e., it will not form a part of the program to deliver electrical stimulation. Alternately, the contribution of the electrode that was below the threshold value may simply be set to zero without adding it to the other electrode's contribution. If, instead, both electrode contributions are above the threshold value, both electrode contributions are kept and each electrode will form part of the program to deliver electrical stimulation. If both electrode contributions are below the threshold value, both are zeroed. In one example, a threshold value of about 0.1 to about 0.3 may be used. In some examples, the threshold value may be about 0.2. In other examples, the threshold may be user configurable or may be dynamic based on tested values for this specific patient or set values for this patient's disease state or reported symptoms. In yet another embodiment, a nonlinear thresholding function may be applied. As an example, the distance ratio might be applied to a sigmoid function and the returned value used to set the contribution.

After the electrode contributions are thresholded, the electrode contributions may be normalized. In one example, the contributions are normalized by determining the electrode(s) with the largest contribution and scaling it to 1.0. The other electrodes are then scaled accordingly with reference to the largest contributor(s). This might be done algorithmically by iterating through all of the electrode contributions for a given zone to find the electrode with the largest contribution, and then iterating through all of the electrode contributions a second time and dividing each by the value of the largest contribution. In this manner, the largest electrode contribution becomes 1.0 (as it was divided by itself) and all of the others scaled appropriately.

Figure 8B:
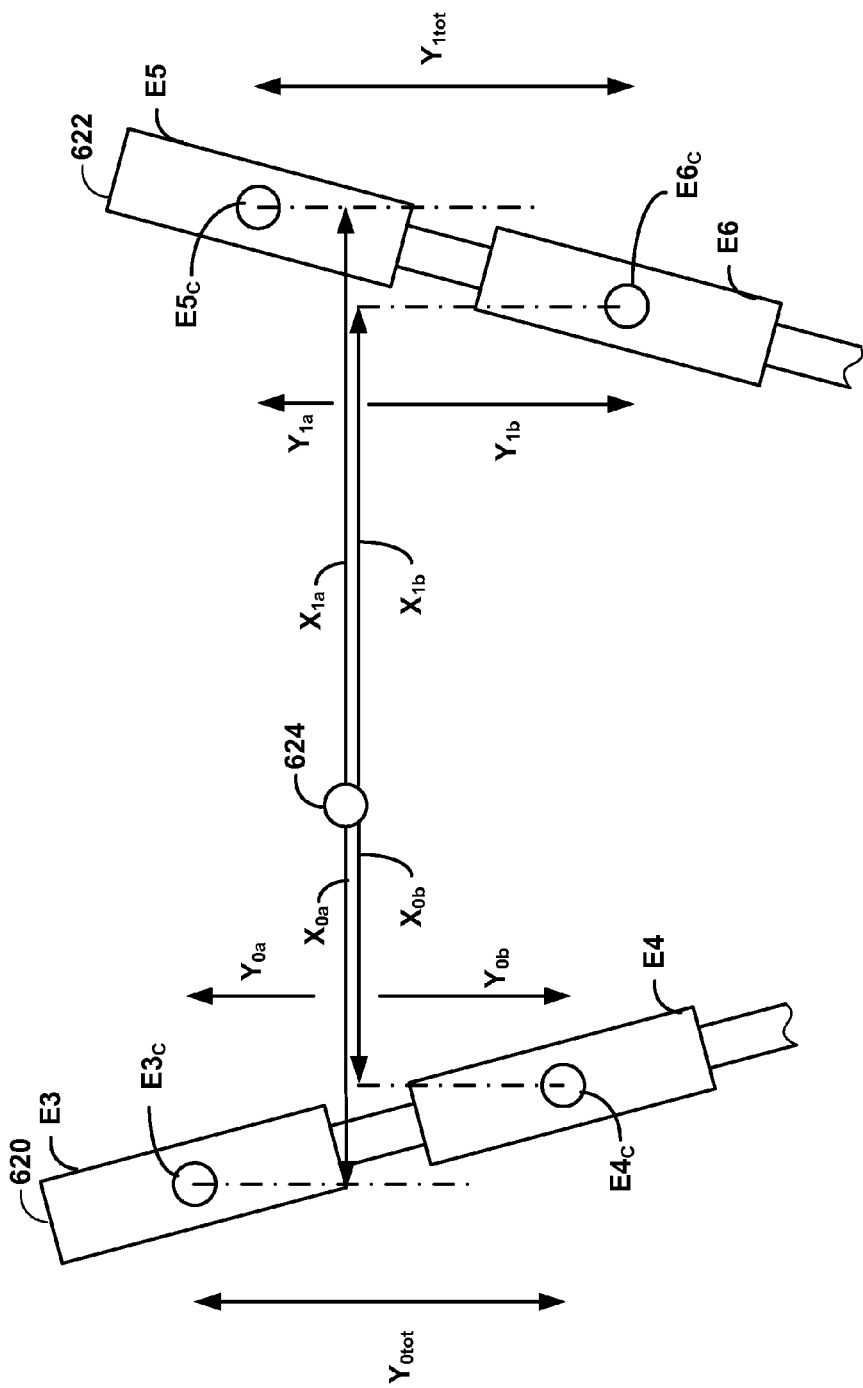
FIG. 8B is a schematic diagram illustrating another example electrode contribution determination using the techniques of this disclosure.

FIG. 8B is a schematic diagram illustrating another electrode contribution determination using the techniques of this disclosure. In contrast to the lead configuration of FIG. 8A, leads 620, 622 in FIG. 8B are angled such that each electrode has a slightly different horizontal value X. For instance, horizontal value $X_{0a}$ is slightly greater than horizontal value $X_{0b}$. In FIG. 8B, the contributions of electrodes E3 and E4 on lead 620 (the left lead) and electrodes E5 and E6 on lead 622 (the right lead) are determined by finding the distance from the selected zone placement point, shown at 624, as a ratio of the total distance between the electrodes, separately in the x and y dimensions. For lead 620, the electrode contributions, which may map proportionally to current amplitude contributions, are determined as follows:

$$E3 = (X_{1a}/X_{0a}+X_{1a})*(Y_{0b}/(Y_{0tot})$$

$$E4 = (X_{1b}/X_{0b}+X_{1b})*(Y_{0a}/(Y_{0tot})$$

And, for lead 622, the electrode contributions are determined as follows:

$$E5 = (X_{0a}/X_{0a}+X_{1a})*(Y_{1b}/Y_{1tot})$$

$$E6 = (X_{0b}/X_{0a}+X_{1a})*(Y_{1a}/Y_{1tot})$$

Figure 9:
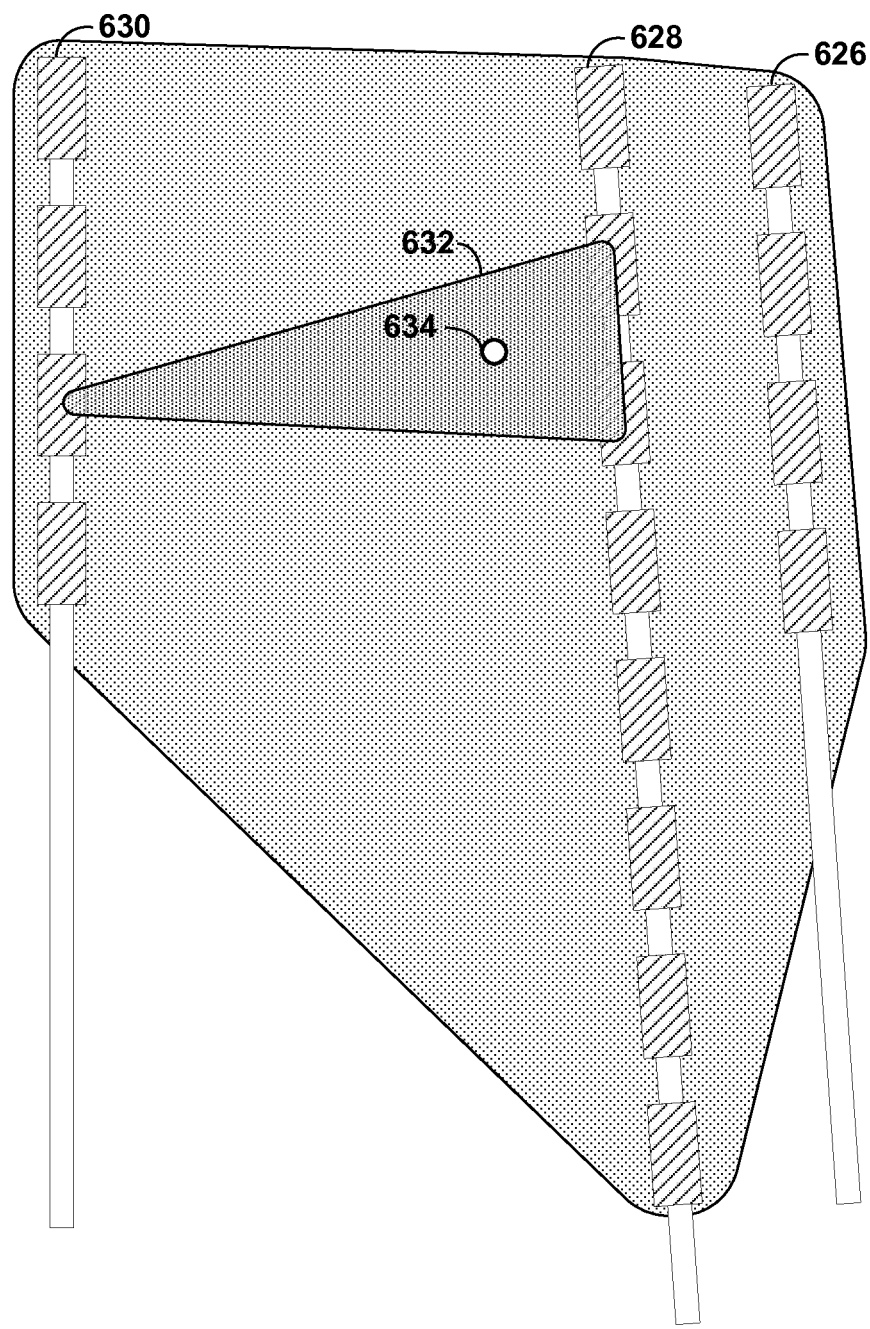
FIG. 9 is a schematic diagram depicting an example configuration of three leads where verification may be needed to ensure that a stimulation zone remains between only two leads.

FIG. 9 is a schematic diagram depicting an example configuration of three leads where verification may be needed to ensure that a stimulation zone remains between only two leads. In particular, FIG. 9 depicts a tripolar configuration. In some example lead configurations, e.g., configurations with three or more leads, a check may be made to ensure that the zone remains between only two leads. In other words, verification may be needed to ensure that the zone does not cross another lead. Referring now to FIG. 9, right-most lead 626 is close to middle lead 628 but far away from left-most lead 630. Stimulation zone 632 is depicted between leads 628, 630. In a lead configuration such as the one depicted in FIG. 9, lead 626 may in fact have closer electrodes to selected zone placement point 634 than lead 630, but lead 626 may be useless for mapping because the user's intent clearly was to generate a stimulation zone between lead 628 and lead 630. In one example, the programmer, e.g., programmer 40, may perform a verification by determining that the four closest electrodes recruited by that particular zone, e.g., zone 632, do not result in crossing a lead. For example, a determination may be made as to whether the line formed by the nearest lead, e.g., lead 628, and the line between zone point 634 and the second lead on which electrodes are recruited, e.g., lead 626, do not intersect. If they intersect, then the mapping is inappropriate and the nearest electrodes on the third lead, e.g. lead 630, should instead be used (even though they are farther than those on lead 626). In FIG. 9, stimulation zone 632 is mapped correctly to the left-most lead, i.e., lead 630, even though electrodes on the right-most lead, i.e., lead 626, are closer to stimulation zone point 634 than the third electrode on the left-most lead, i.e., lead 630.

After the user has placed the zone, e.g., zone 632, on the display, the programmer may generate and display to the user an indication of the extent of the achievable field shape, or indication of zone extent, based upon electrodes that the zone has recruited. It should be noted that the programmer has generally calculated the ASR before the user has placed the zone on the display. In one example, the indication of the extent of the achievable field shape may be determined by the current electrode contributions of the electrodes recruited by this zone. The indication of extent of achievable field shape may allow the user to visually discern the relative contributions of each electrode recruited by the zone. In some examples, the indication of extent of achievable field shape may be accomplished by drawing a low opacity zone wherein a circle of points is drawn over an electrode at a radius scaled to the contribution of that electrode. A convex hull may then be taken of all such circles for all electrodes recruited by the zone, and a polygon or other shape is constructed and drawn. In another example, the extent of achievable field shape may be calculated by finding the electromagnetic field generated by stimulation at the zone's recruited electrodes and applying a threshold to that field to determine the portion to display (i.e. displaying only field strength greater than or less than (for anodes or cathodes) a given threshold). This field strength may be calculated as a voltage gradient, current density, or electric field strength created by the stimulating electrodes. As an example, for electric field, Coulomb's law may be used ($E=1/(4*Pi*\epsilon_0)*Q/r^2$), where the charge Q is the total charge delivered per pulse by each of the electrodes and r is the distance from the electrode to a point in the ASR. In addition to, or instead of, using electromagnetic field strength, the field shape may also be representative of a volume of tissue activated by the electromagnetic fields created by stimulation. In this case, field strengths are first calculated (via Coulomb's law, current densities, voltage gradients, or otherwise) and then the fields are applied to a computational model of neurons. Regions in which the computational model suggests neurons would be activated or inhibited by the fields created by stimulation may then be used to define the field shapes presented on a display to support further optimization.

Figure 10A:
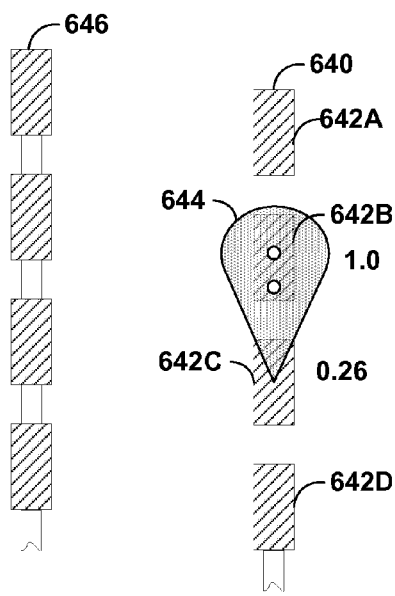
FIGS. 10A-10C are schematic diagrams depicting several example indications of the extent of achievable field shape based upon the electrodes recruited.
Figure 10B:
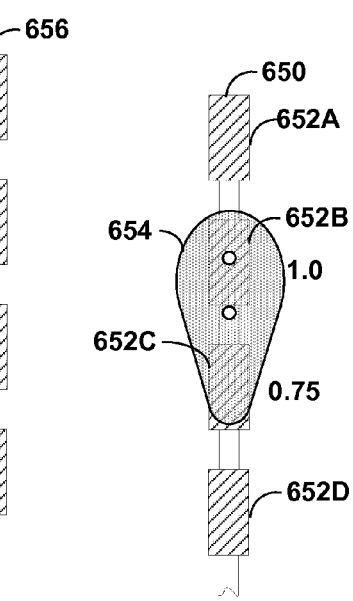
Figure 10C:
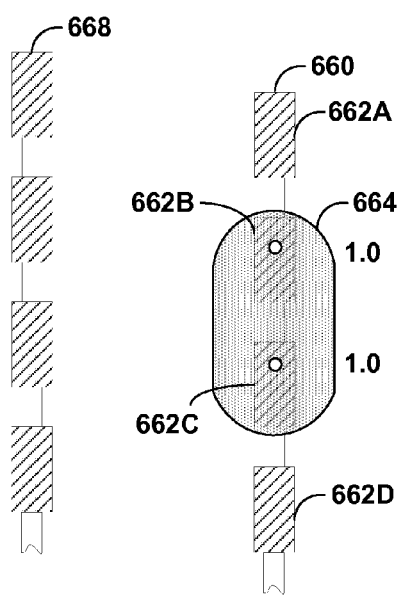

FIGS. 10A-10C are schematic diagrams depicting several example indications of the extent of achievable field shape based upon the electrodes recruited. FIG. 10A depicts an indication of zone extent between two electrodes on the same lead, in particular lead 640 (the right-most lead). The second electrode from the top of the lead, i.e., electrode 642B, has a scaled contribution of 1.0, while the third electrode from the top of the lead, i.e., electrode 642C, has a scaled contribution of 0.26. Such an electrode contribution configuration results in the indication of zone extent shown in FIG. 10A at 644 that envelops electrode 642B with a contribution of 1.0, extends in a narrowing manner to a sharp point that is approximately at the center of electrode 642C, and only partially covers the top portion of electrode 642C with a contribution of 0.26. As seen in FIG. 10A, no electrodes are recruited from lead 646.

FIG. 10B depicts an indication of zone extent between two electrodes on the same lead, in particular lead 650 (the rightmost lead). The second electrode from the top of the lead, i.e., electrode 652B, has a scaled contribution of 1.0, while the third electrode from the top of the lead, i.e., electrode 652C, has a scaled contribution of 0.75. Such an electrode contribution configuration results in the indication of zone extent shown in FIG. 10B at 654 that envelops electrode 652B with a contribution of 1.0, extends in a narrowing manner to a blunted point that is near the bottom edge of electrode 652C, and almost completely covers electrode 652C with a contribution of 0.75. As seen in FIG. 10B, no electrodes are recruited from lead 656.

FIG. 10C depicts an indication of zone extent between two electrodes on the same lead, in particular lead 660 (the rightmost lead). The second electrode from the top of the lead, i.e., electrode 662B, has a scaled contribution of 1.0, and the third electrode from the top of the lead, i.e., electrode 662C, also has a scaled contribution of 1.0. Such an electrode contribution configuration results in the indication of zone extent shown in FIG. 10C at 664 that envelops both electrode 662B and electrode 662C, thereby creating an oblong indication of zone extent that is substantially symmetric about both an x-axis and y-axis drawn through the center of the indication of zone extent. As seen in FIG. 10B, no electrodes are recruited from lead 668.

In FIGS. 10A-10C, each indication of zone extent depicts two small circles. In FIGS. 10A-10C, the top-most circle is the anchor of the zone that the user originally placed. The second circle indicates where the user may click, for example, and stretch the zone, as described in more detail below.

In accordance with certain techniques of this disclosure, a user may also be able to "stretch" a zone, e.g., change the shape of a placed zone. The user may have the ability to change the shape of a zone by directly manipulating on the display screen its indication of zone extent. In one example, a zone may be stretched by clicking with a mouse or touching with a stylus, for example, within the indication of zone extent and then dragging the zone, e.g., the boundaries of the zone. In other examples, the zone may be stretched using control points, a selectable outline, etc.

Figure 11:
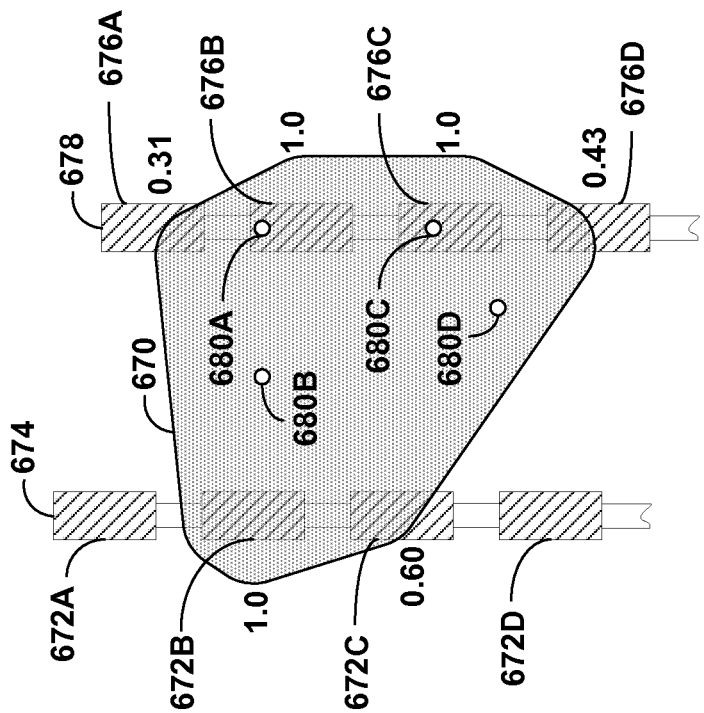
FIG. 11 is a schematic diagram depicting an example indication of zone extent that a user has stretched in accordance with the techniques of this disclosure.

FIG. 11 is a schematic diagram depicting an example indication of zone extent that a user has stretched in accordance with the techniques of this disclosure. A user may have, for example, graphically manipulated, e.g., stretched, the indication of zone extent shown in FIG. 10C at 664 by clicking within the zone to select the zone, and then dragging the boundaries of the zone in order to produce the indication of zone extent depicted in FIG. 11 at 670. As seen in FIG. 11, six electrodes, two electrodes, i.e., electrodes 672B, 672C, on the left lead, i.e., lead 674, and four electrodes, i.e., electrodes 676A-676D on the right lead, i.e., lead 678, have been recruited in order to produce the desired, stretched zone 670. Three of the six electrodes recruited have contributions of 1.0, one on the left lead, i.e., electrode 672B, and two on the right lead, i.e., electrodes 676B, 676C. The indication of zone extent shown in FIG. 11 at 670 completely envelops the electrodes with contributions of 1.0 while the indication of zone extent only partially covers the electrodes with contributions of 0.31 and 0.43 (both on lead 678) and 0.60 (on lead 674).

Shape changes produced by a user stretching the indication of zone extent, e.g., indication of zone extent 670, may include both increases in shape and decreases in shape. Changes produced by stretching may include changes in contribution and/or changes in the number of electrodes recruited by a zone. That is, additional electrodes may be recruited in order to produce the zone, and/or contributions of previously recruited electrodes may be increased or decreased based on the user's stretching of the zone. In one example algorithm, when a user originally places a zone, the point used to calculate electrode recruitment and electrode contributions is stored in a list for that zone. When the user later begins to stretch that zone, a second point is stored in that list, and a second set of electrode recruitment and electrode contributions is calculated.

The two sets of electrode recruitments and contributions may be merged by adding only those that increase or are new to the first set. The resulting shape is drawn from this merged set as the user drags the zone, and then finalized when the user finishes dragging, e.g., mouse up. This process may repeat for additional stretches. For additional stretches, more centers are created and merged in order to create the electrode recruitment and contributions for a zone. In one example, an additional step of culling superfluous centers from the list may be performed by the programmer.

In some example implementations, the centers used to create a zone are shown as circles. For example, FIG. 11 depicts four circles, i.e., circles 680A-680D, used as centers. Using circles may allow a center to be adjusted directly. In other example implementations, the display of the circles may be replaced by either a different control point strategy or automation where the centers are not actually shown and the system automatically picks a "close" center for adjustment if one exists when a user begins stretching, rather than creating a new one.

The centers used to create zones may, in some examples, be stored as metadata for a program by a first programmer within the implanted medical device. By storing the centers as metadata within the implantable medical device, the zones may be accurately recreated on a second programmer at a later programming interaction without the need for data transfer between programmers. However, if a manual editing capability is desired on a per electrode basis, an inverse algorithm may be used to create the zones, e.g., by calculating a minimum set of centers necessary to recreate a particular electrode recruitment and contribution scenario. In some example implementations, the metadata may be additionally, or alternatively, stored within a first programmer and, if necessary, transferred to a second programmer.

Alternately, the centers may be ephemeral, used only during placement or stretching to determine electrode contributions according to distances, and then discarded after the stretch or placement completes. Although this may obviate the need for metadata, the programmer may need to recreate the graphical view of a field shape based only on the electrodes involved and their contributions.

In some example implementations, rather than using circles and centers in order to create the electrode recruitment and contributions for a zone, the programmer may draw a convex hull around all recruited electrodes. The programmer stores the contributions of all electrodes and which electrodes are part of the same zone shape. Then, the programmer redraws the convex hull as needed.

It should be noted that in one example implementation, if a zone is stretched such that it begins to recruit electrodes that are already in use by other zones in the field shape, the stretch may be blocked from extending further. In some examples, the programmer may generate an indication to the user that the stretch is being blocked, e.g., by a sound or by a dialog box or other visual indication on the display screen of the programmer.

In other example implementations, rather than blocking a stretch, the newly recruited electrode(s) may replace or overwrite the existing electrode(s). This implementation may depend on the inverse mapping. That is, the system may need to be able to redefine the zone upon which the zone being stretched is impinging based upon a new set of electrode values, and thus may need to be able to map backwards from such values to centers.

It also should be noted that in some example implementations the system may prevent stretches that would move a zone center outside of the ASR.

In one example implementation, electrodes that fall entirely within the zone shape, or indication of extent, but have not been recruited by the centers by which the zone is defined may be set by the system to each have contributions of 1.0. In the interest of having the fewest centers, it may be desirable to cull those centers that are unnecessary for maintenance of the zone shape. However, this culling may lead to situations on large zone shapes where electrodes are missed.

Figure 12:
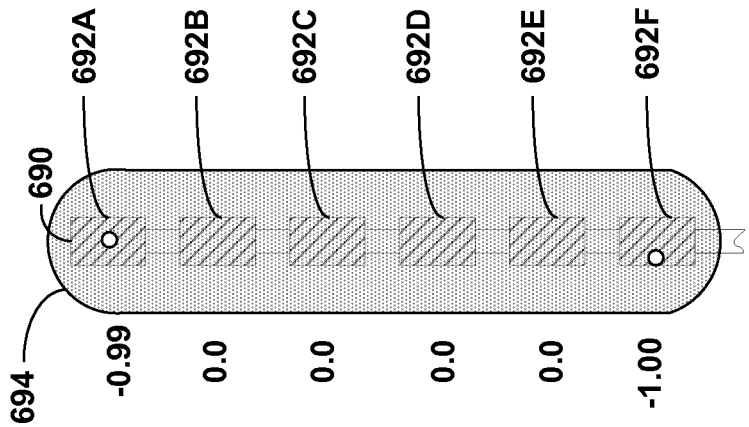
FIG. 12 is a schematic diagram depicting an example indication of zone extent in which electrodes that fall entirely within the zone shape, or indication of extent, but have not been recruited by the centers by which the zone is defined may be set by the system to each have contributions of 1.0.

FIG. 12 is a schematic diagram depicting an example indication of zone extent in which electrodes that fall entirely within the zone shape, or indication of zone extent, but have not been recruited by the centers by which the zone is defined may be set by the system to each have contributions of 1.0. In FIG. 12, six electrodes, namely 692A-692F, on the portion of lead 690 depicted fall entirely within indication of zone extent 694. The system may check all electrodes for inclusion in the particular zone's shape and, if the electrodes are not already recruited, then the electrodes are set to full contributions of 1.0. This may be accomplished by checking whether both the top center and bottom center of each electrode are within the shape defining the zone's extent. In FIG. 12, six electrodes are depicted, namely electrodes 692A-692F, electrode 692A being at the top of FIG. 12, and electrode 692F being at the bottom of FIG. 12. As shown in FIG. 12, indication of zone extent 694 includes all six electrodes. Although shown as 0.0, in accordance with the techniques described above, electrodes 692B through 692E should have electrode contributions of 1.0 because these electrodes are contained within the shape of the zone.

In some cases, the system may allow the user to directly edit the value of an individual electrode. This may cause the system to remap centers and/or recalculate contributions such that a new zone shape, reflecting the newly edited electrode values, can be drawn. In this situation, the contributions of interior electrodes such as 692B-E may be changed from 1.0 subsequent to the creation of the zone.

In accordance with the techniques of this disclosure, a zone placed by a user may also be moved by the user after placement. That is, the user may select one or more zones and move them to a target location. In one example implementation, the system may prevent a user from moving a zone to a target location that is outside of the ASR. In addition, the system may prevent a user from moving a zone to a target location if the target location would result in electrodes being recruited by the zone(s) being moved to overlap those electrodes previously recruited by other zones. In some examples, such moves may be prevented using a method similar to that described above with respect to stretches of a zone colliding with another zone.

In one example, an algorithm may leverage the zone placement logic described throughout this disclosure in order to allow a zone to be moved. For example, a grey dot at the centroid of a zone shape may allow an outline of the zone shape to be dragged and dropped. This is the target location for the move. The system may calculate a move trajectory vector between the starting centroid, e.g., a centroid of the center points that define the first zone, and the ending centroid. The system may then divide that trajectory vector into a number of equal sized steps. Short moves thus have fewer steps, and long moves have more steps. The size of the step may, for example, be determined by the responses of patients to trial stimulation, and thus may be easily configurable. This move vector, and its subdivision into multiple steps, may be shown to the user to increase understanding of what will happen when the move begins. The system may restrict this move vector to directions substantially parallel to the leads (longitudinal moves) or substantially orthogonal to the leads (transverse moves) to better match clinical practice or to attempt to preserve zone shape at the end of the move.

The user may then step the move forward step by step. At each step, the step vector is applied to each center of the zone being moved as a translation, and the zone shape is recalculated from the new centers. This continues (forward or backward) until the target location is reached, the user elects to end the move, or the user returns the zone back to its starting location. The user may control this move with step sequence controls (forward, backward), with automated sequence controls (play, pause) which apply steps on a fixed or adjustable time basis, or by selecting a desired step from a list or by indicating the desired step on the subdivided move vector.

In some examples, programmer 40 may display the movement of the zone as a "film-strip." That is, for each step of the move, programmer 40 may display a representation of zone in a "thumb-nail" window, thereby forming a "film-strip" of the move.

Both single zone moves and compound zone moves, e.g., multiple zones or all zones moving simultaneously, are supported using the techniques of this disclosure. In some example implementations, it may be desirable to apply the transition steps such that minimum zone to zone interference occurs. This may mean that an interfering zone is first moved independently such that it no longer interferes, followed by movement of the zone which was previously interfered with.

Another example implementation sequences the compound moves by applying a series of steps to the zone at the leading edge of the move until the zone clears electrodes sufficient to move the next zone.

As mentioned above, the techniques of this disclosure allow an indication of zone extent to be stretched or moved on the display. It may be desirable in some examples to control the rate of change of the stretches and moves. In one example, the system may create target shapes or locations rather than stretching or moving in real time. Then, the system may allow the user to move towards that target shape or location at a controlled rate. The rate of change of a stretch or move may range from single steps, one or more moderate rates, to jumping to the target directly.

It should be noted that, in some examples, stretching a zone may cause a target shape to be created without immediately changing stimulation. Similarly, moving a zone may cause a target shape at the final location to be created without immediately changing stimulation. Rather, a user may view the stretched or moved zone, and then separately activate a program button to cause the parameters associated with the zone to be applied for delivery of electrical stimulation by the stimulator. In this sense, the response of the stimulation delivered by the stimulator may not be immediate or continuous in some examples. In other examples, the programmer may cause the stimulator to respond to the stretching or movement in a substantially immediate and/or continuous manner.

In some examples, the user may receive an indication of the extent of stimulation that will be active once the target shape or location is achieved. For example, the actual or current stimulation may be shown along with the future target stimulation. Display of the target stimulation may include one or more of the conditions that may be displayed for the actual or current stimulation, e.g., contributions of electrodes, intensity of zone, and the like.

Figure 13:
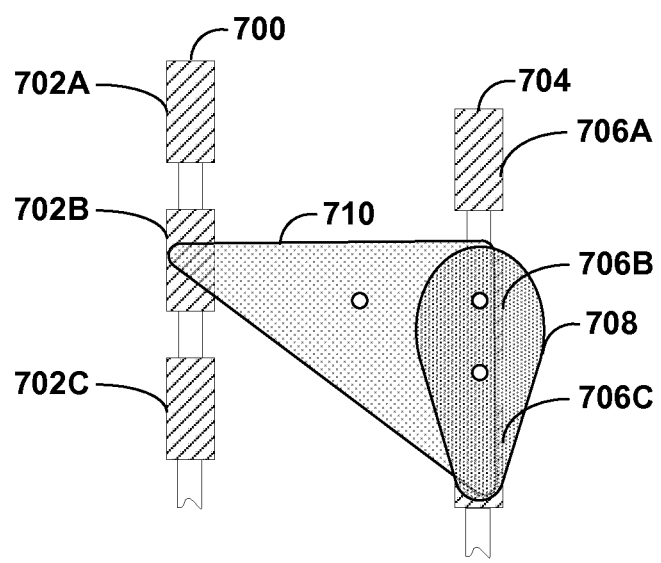
FIG. 13 is a schematic diagram depicting an example indication of a target stretch in accordance with the techniques of this disclosure.

FIG. 13 is a schematic diagram depicting an example indication of a target stretch in accordance with the techniques of this disclosure. In FIG. 13, portions of two leads are depicted, each portion having three electrodes. In particular, lead 700 includes electrodes 702A-702C and lead 704 includes electrodes 706A-706C. The current zone shown at 708 is depicted as extending from electrode 706B on lead 704 to another electrode, namely electrode 706C on the same lead. The indication of the target stretch is depicted at 710 as extending from electrodes 706B, 706C on lead 704 to middle electrode 702B on lead 700.

In some examples, the system may indicate the size of the steps that will be taken when shifting from a currently defined zone to a defined target zone. The size of the steps may be fixed or dynamic, varying based on the length of the move, the direction of the move, the response of the patient, the leads' location relative to physiology, the leads' distance from each other or anatomical structures, or other factors.

When a zone exists with an active target, the system may display means for the user to control the rate of progress towards the target, including single step, moderate rate, and "jump to target" capabilities. Allowing the user to control the rate of progress may allow the user to move forwards and backwards in the moving sequence. This may be desirable in the event that an uncomfortable stimulation results from a transition. Allowing a user to move backwards, for example, in the moving sequence may be more desirable than zeroing the electrode intensities or taking other drastic action.

In some examples, the user may be able to set stretch targets on multiple zones and then control progress towards them simultaneously. For example, a user may want to set a stimulation stretch target and at the same time a guard stretch target and then shift towards them together. This may be accomplished, for example, as a multiple selection move rather than a stretch. However, performing this as a stretch rather than a move may provide additionally capability, such as allowing rotations of stimulation, asymmetric moves, and the like. In other examples, a stretch may be broken into a plurality of individual steps that may be accessed randomly by the user or in sequence by the user, e.g., like a chapter selection.

In accordance with certain techniques of this disclosure, the system may also provide the user with the ability to change the intensity of one or more zones. A zone's intensity is equivalent to the intensity of its strongest individual electrode. In one example implementation, changes to a zone's intensity may be unitless, e.g., as a percentage, while in other implementations the changes may be represented in absolute terms, e.g., milliamps of current output. Some example implementations may indicate changes in a zone's intensity as both a percentage and in absolute terms.

In some examples, the user may have the ability to change the intensity of a selection of zones simultaneously, where the selection includes all active zones. For example, the system may include a "master amplitude" or "master intensity" control that allows the user to change the intensity of all zones simultaneously. In one example, it may be desirable to use a percentage or other unitless basis if a user is changing the intensity of multiple zones simultaneously.

The system may scale independent electrode currents in proportion to electrode contributions as a user changes the intensity for a zone. For example, if a zone's intensity is set to 10.0 mA, and the zone has a first electrode at full, i.e., 1.0, contribution and a second electrode at 0.5 contribution, the system may set the first electrode to 10 mA as a desired output current and the second at 0.5*10 mA=5.0 mA of desired current.

In one example, the system may graphically display the current intensity of a zone. The display of zone intensity may reflect the relative electrode contributions within that zone. In some example implementations, graphical display of the current intensity of a zone may be accomplished, for example, by drawing a higher opacity, scaled version of the zone contribution indication, e.g., using a scale transform of normalized intensity (current intensity/max intensity) in the x and y dimensions from the centroid of the shape. In addition, in some examples, the system may provide textual indication of intensity in using actual current levels or it may be unitless, e.g., percentages.

In another example, the system may draw the intensity as starting over each electrode, scaled to contribution, and then morph the individual electrodes' intensity representations into each other as intensity grows large enough to cause stimulation to occur between electrodes or between leads. This may be accomplished in some example implementations by drawing small intensities as substantially symmetric circular shapes over each electrode but then stretching each circular shape towards the other contributing electrodes as in proportion as intensities increase towards max. As individual stretched shapes begin to overlap, the programmer would combine them and then continue to stretch the combined shape towards any remaining non-combined electrode shapes. An alternate means of achieving this effect in a design using the electromagnetic field to draw indications of field extent would be to apply a second threshold to the calculated field, thus drawing smaller shapes (the peaks of the field contours) at low intensities, shifting the second threshold towards the first threshold as intensity increases, until the intensity reaches max, the thresholds reach the same value, and the actual intensity shape matches the achievable extent of stimulation. Other methods include using opacity, saturation, or some other characteristic of the contribution indication to show intensity changes.

The master amplitude or master intensity of the stimulation generator, e.g., stimulation generator 60A, may be set such that the output of the highest contributing electrodes of the highest intensity active zone is set to full output, e.g., $64/64^{th}$s, for an example implementation with a resolution of 1/64. In other words, in an example configuration in which one or more of 64 parallel current regulator branches may be used to implement each current regulator (i.e., a resolution of 1/64), stimulation generator 60A may be set such that, for each of the highest contributing electrodes of the highest intensity active zone, all 64 parallel current regulator branches are used. All other active electrodes may then be scaled so as to match as closely as possible their desired output amplitude, e.g., zone intensity*contribution. It should be noted that changes to the intensity of one zone may change the settings of all other active zones. If the master amplitude changes, then the system may need to recalculate the fractions of contribution for all other active electrodes based on their desired values. Due to the resolution limit of 1/64 in some example implementations and the potentially large dynamic range of output current, e.g., 0.1 mA to 35 mA, in some configurations the desired amplitude for a given electrode may be difficult to achieve.

Recalculating the fractions of contribution for all other active electrodes based on their desired values may be accomplished, in one example, by finding the maximum desired amplitude across all active stimulation or guard zones in this field shape, including the housing electrode, which may be in use to balance other stimulation. The master amplitude may then be set to this value. Each electrode then has a ratio, e.g., in $64^{th}$s for implementations where the resolution is 1/64, that is calculated from its desired amplitude and the master amplitude that was set. It may be desirable to analyze the worst case, i.e., where settings of all active zones change, and provide to the user an indication of the difference between the desired amplitude and the achievable amplitude. In some example implementations, the system may provide an indication to the user, e.g., a dialog box or other visual indication, when the actual amplitude delivered will differ from the desired amplitude by more than a certain percentage.

In accordance with certain techniques of this disclosure, the system may also attempt to balance stimulation with changes to the housing electrode as the intensity of a stimulation zone is change. For example, if a stimulation zone is added when no guard (anode) zones are active, the system may set the housing electrode as the active guard zone, i.e., a unipolar configuration. By way of specific example, assume a single stimulation zone exists with two electrodes recruited having contributions of 1.0 and 0.5. If the zone's intensity is increased from 0 to 10 mA, then the system may activate the housing electrode as an anode and increase its intensity from 0 to 15 mA such that the sum of the products of the stimulation zone intensity and electrode contribution equal the intensity of the case, e.g., (1.0*10 mA)+(0.5*10 mA)=15 mA).

Figure 15:
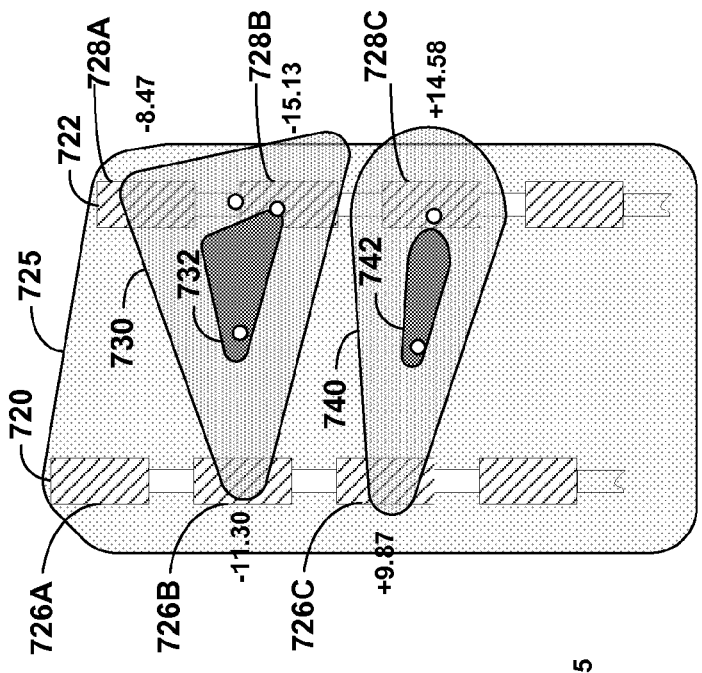
FIGS. 14 and 15 are schematic diagrams depicting an example of balancing electrical stimulation currents with changes to the housing electrode stimulation parameters when a guard zone is added.
Figure 14:
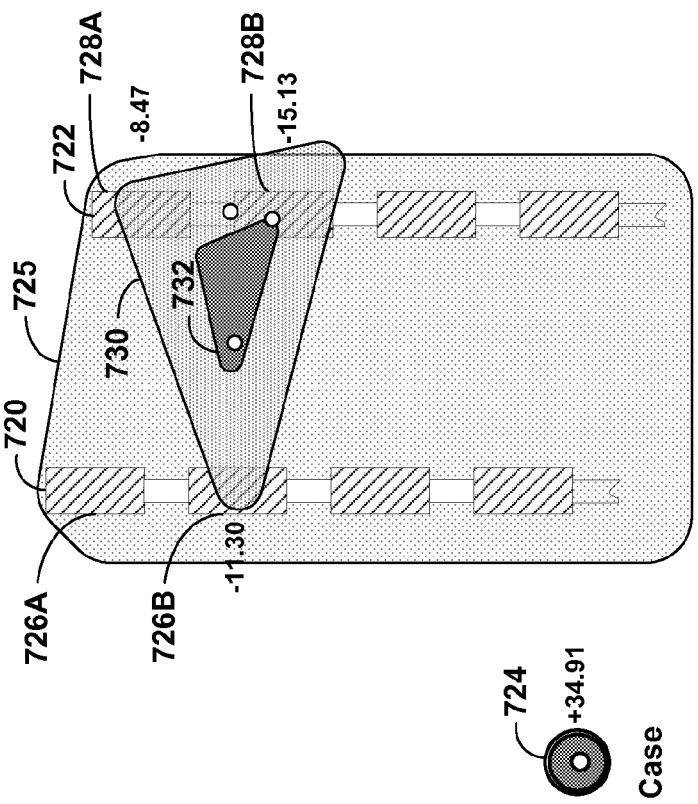

FIGS. 14 and 15 are schematic diagrams depicting an example of balancing electrical stimulation currents with changes to the housing electrode stimulation parameters when a guard zone is added. In FIG. 14, a portion of two leads, namely leads 720, 722, is shown, as well as housing electrode ("case") 724. Leads 720, 722 are surrounded by ASR 725. Three lead electrodes are active, in particular, electrode 726B on lead 720 and electrodes 728A, 728B on lead 722. These three active electrodes may be used to create stimulation zone 730 with an intensity shown graphically at 732. The sum of the lead electrode current (here, cathodal current) equals the housing electrode current (8.47 mA+11.30 mA+15.13 mA=34.91 mA, with some rounding error). If a guard zone is added in the stimulation region when the device is in unipolar mode, the system may balance stimulation, using the techniques of this disclosure, by automatically decreasing the intensity of the housing electrode's zone such that its output added to the other active guard zones equals the current output of the stimulation zones.

FIG. 15 depicts the configuration shown in FIG. 14, with the addition of guard zone 740 with an intensity shown graphically at 742 placed between electrode 726C on lead 720 and electrode 728C on lead 722. As intensity 742 of newly added guard zone 740 on the leads increases, the intensity of the housing electrode zone, depicted graphically at 744, may decrease from its value of 34.91 mA in FIG. 14 to a value of about 10.45 mA in order to maintain balance (8.47 mA+11.30 mA+15.13 mA=9.87 mA+14.58 mA+10.45 mA).

Thus, in some example implementations, as the shape of a stimulation zone is changed, the system may attempt to balance stimulation with changes to the housing electrode. Any change in shape to a stimulation zone that causes a net difference in total contribution across zones, e.g., most stretches, may also require balancing to be recalculated.

It should be noted that in one example, if an increase in a stimulation zone's intensity would cause the housing electrode to exceed its maximum output, any further increase may be blocked. In addition, if an increase in a guard zone's intensity would cause the housing electrode intensity to reach zero, any further increase may be blocked.

In some examples, if a stimulation zone's intensity is decreased, the system may scale all active guard zones downward in order to maintain balance. In another example, the housing electrode may be preferentially decreased until it is zero, and then other guard zones may be scaled downward such that balance is maintained. In this manner, the system may transition from an omnipolar configuration to a bipolar configuration while decreasing. In yet another example, the housing electrode may be preferentially decreased until it is zero, and then other decreases may be blocked. In such an example, the programmer may generate an indication to the user that the system has blocked further reduction and any further reductions must be performed manually by the user rather than by automatic scaling. In another example, the system may automatically add or remove zones at lead locations or at stimulation levels that will be likely to be subtherapeutic in effect in order to maintain balance during a user driven adjustment. An example of a non-therapeutic location may be the addition of an anode at a position on the lead at least several electrodes away from a nearest active electrode. An example of a subtherapeutic stimulation level might be one that is less than 10% or 20% of the lowest zone intensity currently in effect.

In some example implementations, the system may provide an indication to the user of achievable stimulation intensities for the zones selected for intensity change given the constraints of balancing and maximum output. The control used for stimulation intensity changes may show this interlock dynamically in one example. Alternately, the system may notify the user that a desired change cannot be achieved, and then provide guidance to the user on how to proceed. For example, if intensity changes are blocked do to an electrode limit being reached, the system may notify the user of the condition and provide prescriptive instructions.

Figure 16:
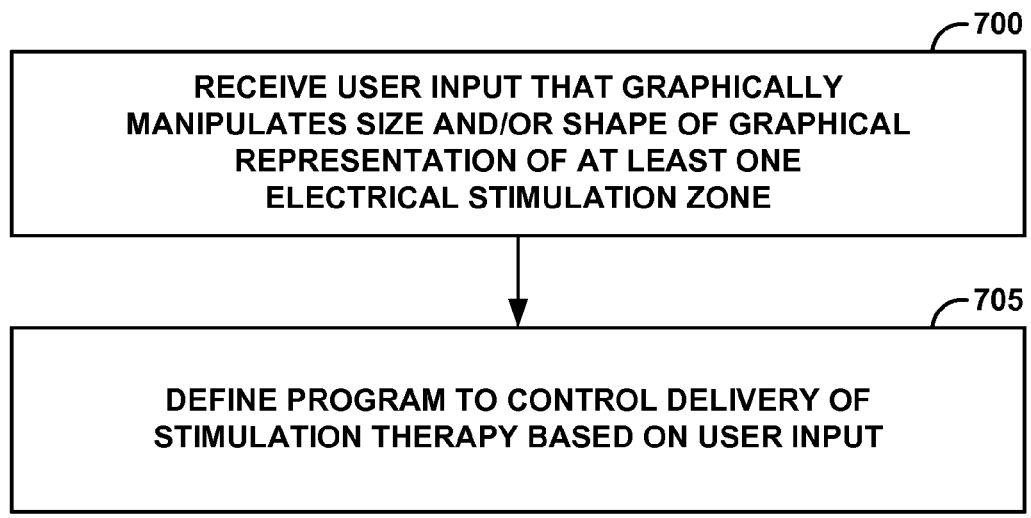
FIG. 16 is a flow diagram illustrating example operation of a programmer using zone-based programming in accordance with the techniques of this disclosure.

FIG. 16 is a flow diagram illustrating example operation of a programmer using zone-based programming in accordance with the techniques of this disclosure. In FIG. 16, a programmer, e.g., programmer 40 and in particular processor 53, receives user input that graphically manipulates at least one of a size and a shape of graphical representations of one or more electrical stimulation zones displayed on the programmer (700). The user may use a mouse or stylus, for example, to place a stimulation zone or guard zone on the display, e.g., display screen 500, of programmer 40. The user may graphically manipulate the size and/or shape of the graphical representation of the zone by moving, shrinking, or expanding the zone after the zone has been placed, e.g., by using a stylus to touch on a border, i.e., an outer perimeter, or an area near the border, of the stimulation zone, and drag it inward or outward to resize the stimulation zone. In addition, the user may adjust the intensity of the zone using the programmer, e.g., using a stylus to adjust a slider bar or arrow keys on the programmer. Processor 53 may rate control any zone stretches or zone moves. Based on the user input, programmer 40, in particular processor 53, may define a program to control delivery of electrical stimulation therapy to a patient (705). For example, in order to define the program, the processor may define, without user intervention, at least one electrode on at least one lead to deliver at least a portion of the electrical stimulation therapy, and determine, without user intervention, an electrical stimulation contribution of the at least one defined electrode to the at least one stimulation zone.

FIGS. 17-20 are schematic diagrams illustrating example user interfaces presented by the programmer of FIG. 4. As described in detail below, FIGS. 17-20 graphically depict a sequence of user inputs in which a user creates a zone, e.g., a stimulation zone, stretches the zone in a first direction, stretches the first zone in a second direction, and then stretches the zone in a third direction. Each stretch may create a new center by which the zone is defined, and the new centers may then recruit more electrodes.

Figure 17:
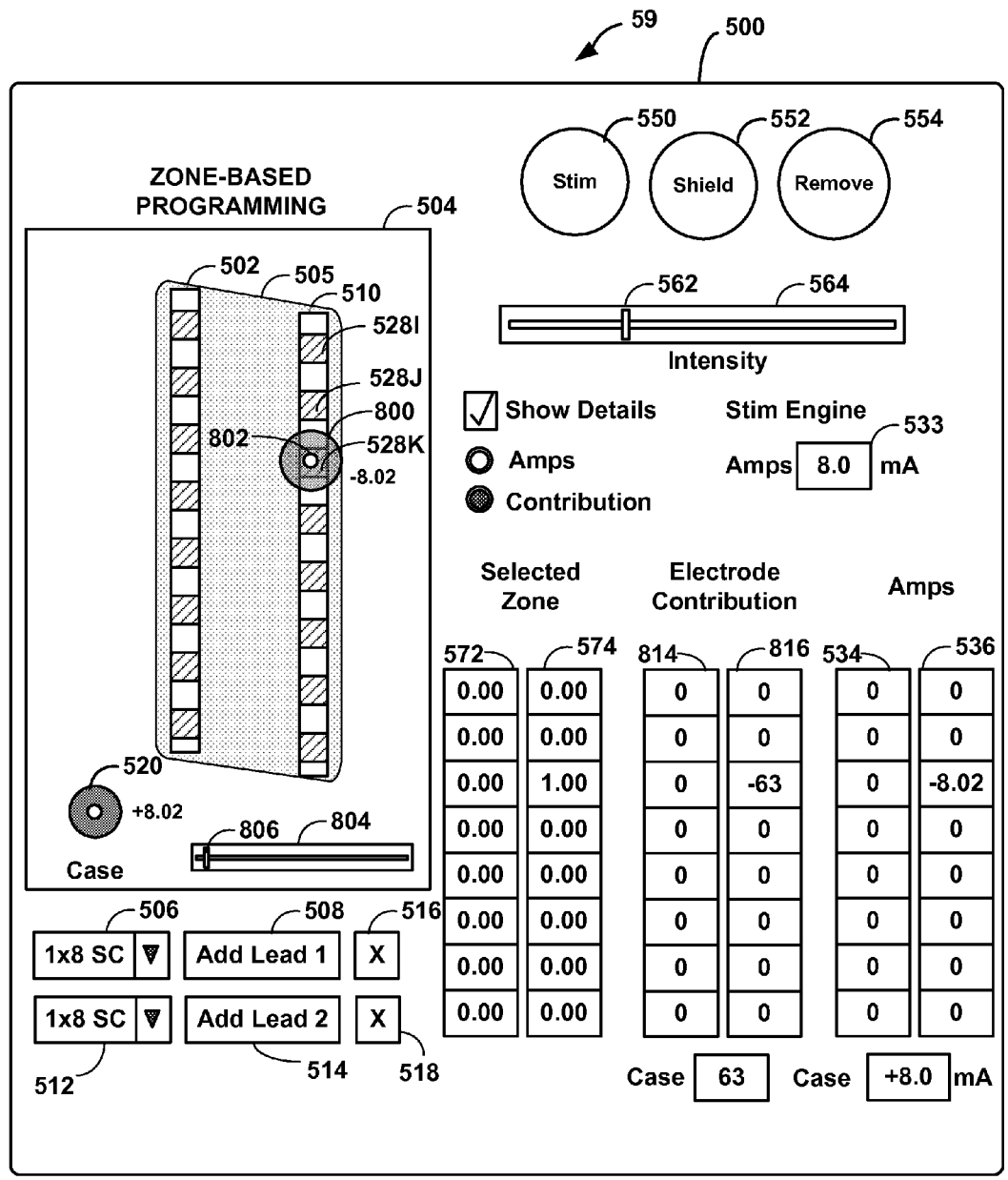
FIGS. 17-20 are schematic diagrams illustrating example user interfaces presented by the programmer of FIG. 4.

FIG. 17 depicts user interface 59 provided by a programmer, e.g., programmer 40, after a user has placed a zone. In other words, user interface 59 is shown displaying a graphical representation of a stimulation zone, namely stimulation zone 800. As described above with respect to FIG. 6, user interface 59 includes stimulation icon 550, shield icon 552, and removal icon 554 that may be used to create a desired stimulation zone(s), as will be described in more detail below. User interface 59 includes display screen 500. A user has added first lead 502 and second lead 510 to window 504 as described in detail above with respect to FIG. 6. As depicted in FIG. 17, each lead 502, 510 has a 1×8 configuration, and the user has created first zone 800 with center 802 on electrode 528K of lead 510 within ASR 505. Thus, the programmer, e.g., programmer 40, displays a graphical representation of stimulation zone 800 via a user interface, e.g., user interface 59. Based on the Selected Zone Intensity as set by indicator 562 of horizontal scroll bar 564, the stimulation current amplitude of zone 800 is −8.02 mA, as indicated in window 504 adjacent electrode 528K, as well as in array 536. Again, the Selected Zone Intensity is used to scale the electrode contributions of electrodes automatically selected to create stimulation zone 800, for example, by the desired intensity to generate stimulation current amplitudes. FIG. 17 further depicts case electrode 520 sourcing 8.02 mA, thereby balancing the stimulation current sunk by electrode 528K. In some examples, window 504 may further include horizontal scroll bar 804 with indicator 806, which may allow a user to zoom the leads in window 504 in and out to modify the resolution of the leads. Modifying the resolution of the leads may facilitate access to the leads via a finger, stylus, or other pointing media.

In some example implementations, programmer 40 allows a user to control case electrode 520. For example, programmer 40 includes an option that allows a user to control whether case electrode 520 is used at all. In other words, a user may prevent the case electrode from being used to source or sink current. In another example, programmer 40 allows a user to set case electrode 520 as a preferential electrode. If selected as a preferential electrode, then the system may attempt to balance any changes in stimulation by first modifying the current sourced or sunk by the case electrode before attempting to modify any electrodes, e.g., anodes, on one or more leads. In another example, programmer 40 allows a user to set a maximum limit for case electrode 520 to source or sink in order to prevent stimulation, for example, at the implant site of the medical device.

Figure 18:
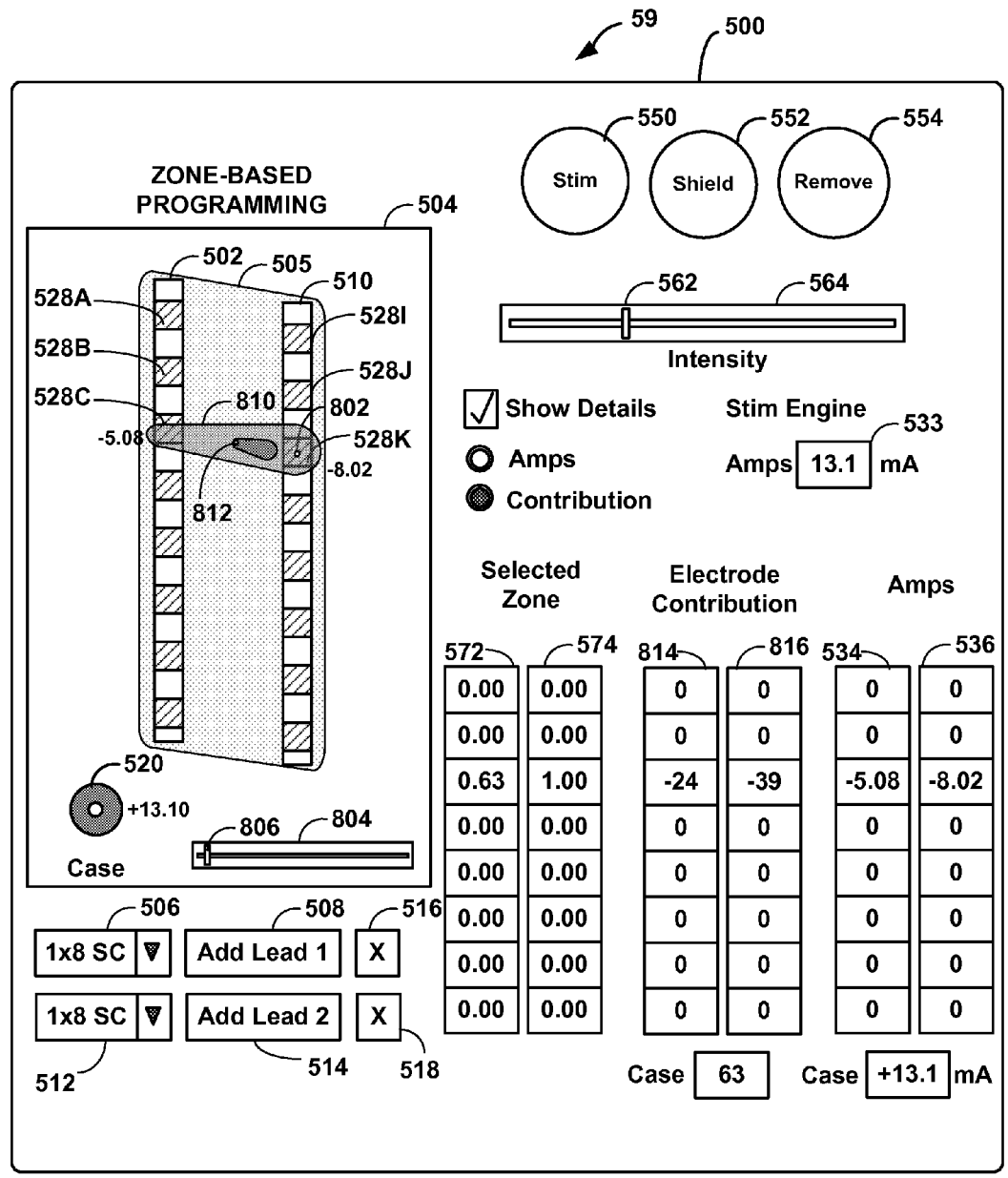

FIG. 18 depicts user interface 59 provided by a programmer, e.g., programmer 40, after a user has graphically manipulated the graphical representation of the zone initially placed in FIG. 17. In FIG. 18, the user has graphically manipulated the graphical representation of stimulation zone 800 of FIG. 17 by stretching zone 800 transversely, thereby creating a new stimulation zone 810 within ASR 505. The stretch has created a new center 812 such that zone 810 is now defined by two centers, namely centers 802 and 812. Newly created center 812 has recruited one other electrode, i.e., electrode 528C from lead 502, to generate stimulation zone 810. As seen in array 572, newly recruited electrode 528C has an electrode contribution of 0.63, and when scaled by the stimulation current amplitude of 8.02, results in a current amplitude of −5.08 mA, as indicated in window 504 adjacent electrode 528C, as well as in array 534.

In order to generate the electrode contributions for the zone, e.g., 0.63 and 1.00 for electrodes 528C, 528K in FIG. 18, the contributions for each center are determined separately, as described above with respect to FIGS. 8A and 8B, and then merged. For each center created after the first center created, e.g., for center 812 in FIG. 18, merging may be accomplished by, for example, determining whether the new center's contributions are for new electrodes, i.e., those electrodes that were not recruited by the first center created, or are greater than those generated by the first center created. In either of these cases, the contribution is added to the list of contributions for the zone. This process may be repeated for each center to generate the total list of contributions for the zone.

In order to achieve this stimulation current and remain balanced, the system automatically, i.e., without user intervention, configures the case, i.e., housing electrode, to source 13.10 mA of current (−5.08 mA+−8.02 mA=−13.10 mA). As a result, the master amplitude of the system increases to 13.10 mA, as shown in current window 533. For the example implementation shown in FIGS. 17-20, the system has a resolution of 1/64. As such, electrode 528C has a contribution of 5.08 mA/13.10 mA, or 24/64, and electrode 528K has a contribution of 8.02 mA/13.10 mA, or 39/64. Electrode resolution is depicted in arrays 814, 816.

Figure 19:
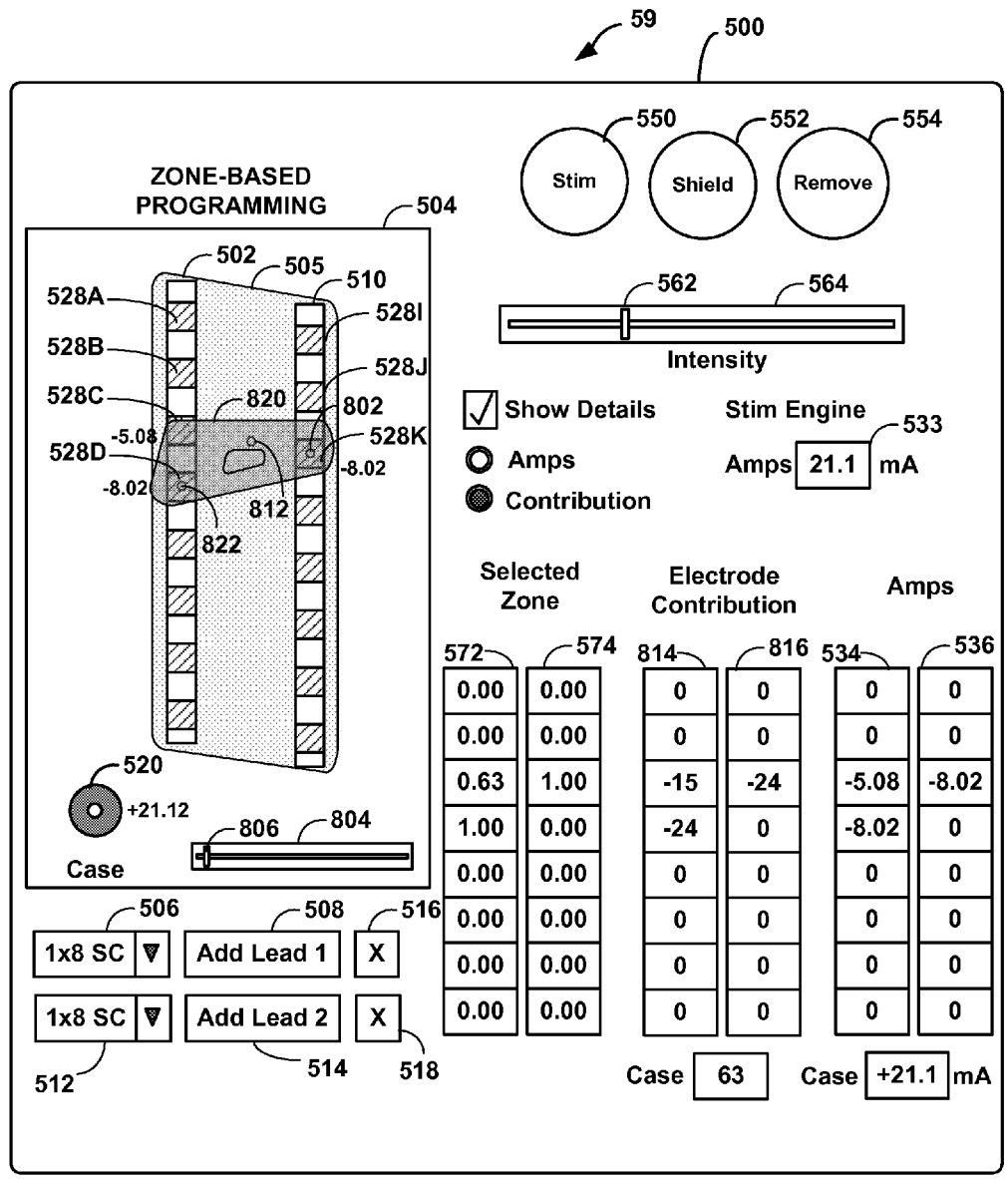

FIG. 19 depicts user interface 59 provided by a programmer, e.g., programmer 40, after a user has graphically manipulated the graphical representation of the zone depicted in FIG. 18. In FIG. 19, the user has graphically manipulated the graphical representation of stimulation zone 812 of FIG. 18 by stretching zone 812 transversely, but with a longitudinal component as well, thereby creating a new stimulation zone 820. The stretch has created a new center 822, located on top of electrode 528D of lead 502, such that zone 820 is now defined by three centers, namely centers 802, 812, and 822 within ASR 505. Newly created center 822 has recruited one other electrode, i.e. electrode 528D from lead 502, to generate stimulation zone 820. As seen in array 572, newly recruited electrode 528D has an electrode contribution of 1.00, and when scaled by the stimulation current amplitude of 8.02, results in a current amplitude of −8.02 mA, as indicated in window 504 adjacent electrode 528D, as well as in array 534.

In order to achieve this stimulation current and remain balanced, the system automatically, i.e., without user intervention, configures the case, i.e., housing electrode, to source 21.12 mA of current (−5.08 mA+−8.02 mA+−8.02 mA=−21.12 mA). As a result, the master amplitude of the system increases to 21.12 mA. As such, electrode 528D has a contribution of 8.02 mA/21.12 mA, or 24/64, as does electrode 528K. Electrode 528C has a contribution of 5.08 mA/21.12 mA, or 15/64. Electrode resolution is depicted in arrays 814, 816.

Figure 20:
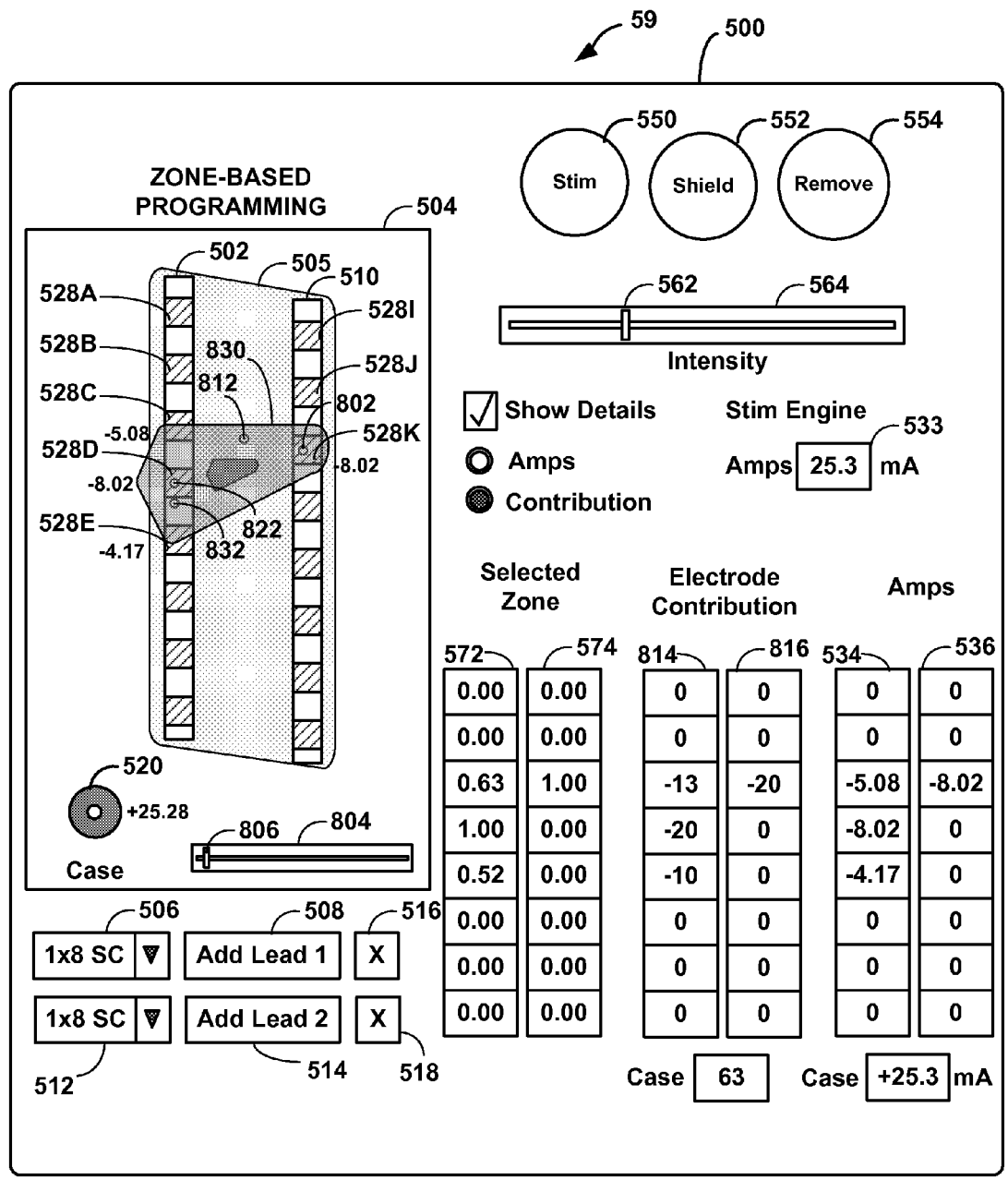

FIG. 20 depicts user interface 59 provided by a programmer, e.g., programmer 40, after a user has graphically manipulated the graphical representation of the zone depicted in FIG. 19. In FIG. 20, the user has graphically manipulated the graphical representation of stimulation zone 820 of FIG. 19 by stretching zone 820 longitudinally, thereby creating a new stimulation zone 830 within ASR 505. The stretch has created a new center 832, located between electrodes 528C and 528D of lead 502, such that zone 830 is now defined by four centers, namely centers 802, 812, 822, and 832. Newly created center 832 has recruited one other electrode, i.e. electrode 528E from lead 502, to generate stimulation zone 830. As seen in array 572, newly recruited electrode 528E has an electrode contribution of 0.52, and when scaled by the stimulation current amplitude of 8.02, results in a current amplitude of −4.17 mA, as indicated in window 504 adjacent electrode 528E, as well as in array 534.

In order to achieve this stimulation current and remain balanced, the system automatically, i.e., without user intervention, configures the case, i.e., housing electrode, to source 25.28 mA of current (−5.08 mA+−8.02 mA+−8.02 mA+−4.17 mA=−25.28 mA, with some rounding error). As a result, the master amplitude of the system increases to 25.28 mA. As such, electrode 528E has a contribution of 4.17 mA/25.28 mA, or 10/64. Electrode 528C has a contribution of 5.08 mA/25.28 mA, or 13/64. Electrodes 528D and 528K each have a contribution of 8.02 mA/25.28 mA, or 20/64. Electrode resolution is depicted in arrays 814, 816.

In an example implementation using the techniques of the disclosure, user programmer 40 may be used to define one or more therapy regions to which stimulation may be applied by implantable stimulator 34. The stimulation may be applied using previously-defined lead placements or by defining lead placements. Multiple regions may be defined by the user, and for each region one or more leads may be used to deliver stimulation therapy. In one example, a lead may be used to provide stimulation therapy to one or more regions.

The user may graphically define one or more desired stimulation regions using user interface 59. User interface 59 may allow a user to view a combined anatomical representation, e.g., an image, of the region where the leads may be implanted and graphical layer representing placement of the leads. The anatomical representation of the region may be retrieved from the implantable stimulator 34 where it may have been stored during a previous session or may be captured by an image capturing device during the current session.

An image capturing device may be used to capture an image of the electrode placement for each of the therapy regions. The image capturing device may be a camera built into the programmer 40 and may be controlled by user interface 59 or may have its own control panel. Alternatively, the image capturing device may be a camera connected to the programmer 40 via an interface, such as a universal serial bus (USB) interface network link, or industry standard interface such as a Digital Imaging and Communications in Medicine (DICOM) standard interface.

A captured image may be manipulated by functions such as, for example, zooming, rotating, panning, cropping, and placing annotations on the image. The image may be compressed and other functions such as, cropping and converting to gray scale, for example, may be used to further reduce the size of the image. Metadata may be also associated with the image to enable a subsequent user to retrieve information regarding the region, the applied therapy, and other information related to the patient and the therapy received. The image may then be used to define therapy for a current session, or may be stored in the stimulator 34 for subsequent retrieval for future therapy.

The user may obtain an image by, for example, making a selection on user interface 59 to capture a screen shot of the image as it appears on user interface 59. The user may also capture the image using the image capturing device by obtaining a digital photograph off of the screen or a print out of the screen of an imaging machine, e.g., a fluoroscopy machine, which may be connected to the programmer 40. The captured image may be an image, produced by a fluoroscopic imaging device, for example, and may be a still or a moving image. The captured image may also be from an imaging modality that shows neural tissue directly, such as an MRI or fMRI. In this case, the structures of interest for stimulation (spinal cord, dorsal roots, etc.) can be visualized directly and not just inferred from bony structures as in a fluoroscopy. Additionally, imaging modalities such as these would allow the user to rotate the viewing plane in 3 dimensions to better visualized dorso-ventral placement of leads, depth of stimulation, or other aspects not visible in two dimensions.

The captured image may then be manipulated by the user for therapy application. The user may define multiple regions and the lead placement in the captured image. For each region, the user may define a set of leads to use for application of therapy to the region. The user may scale, stretch, move, or rotate the lead images to match the lead placement in the image of the therapy. Additionally, the user may perform other functions such as, for example, zooming, panning, and moving within the image, and adding annotations.

In one example implementation, the therapy may be defined by specifying an electrode combination and specifying parameters associated with the leads and/or electrodes. In another example, the therapy may be defined using zone-based programming, as described above, through which the user may graphically define desired stimulation fields and may also define desired therapy intensity. Based on the defined stimulation field and therapy intensity, the contribution of each electrode used in the region may be automatically determined.

As mentioned above, paddle leads may also be used to implement various techniques of this disclosure. Example paddle leads are depicted in FIGS. 21A-21B.

Figure 21A:
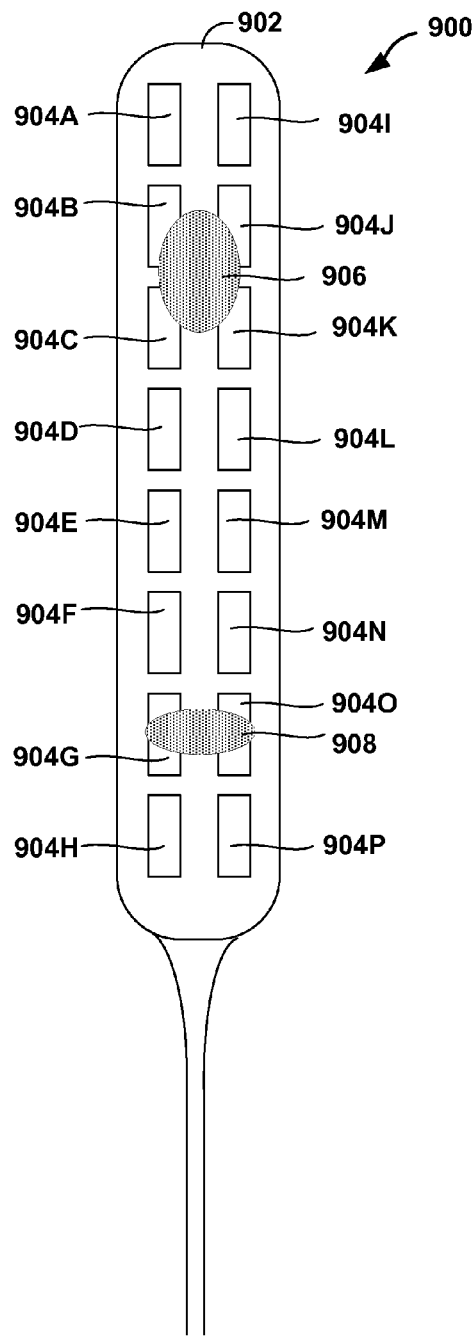
FIGS. 21A-21B are schematic diagrams illustrating top views of example paddle leads having a plurality of electrodes positioned on at least one surface of the paddle lead.
Figure 21B:
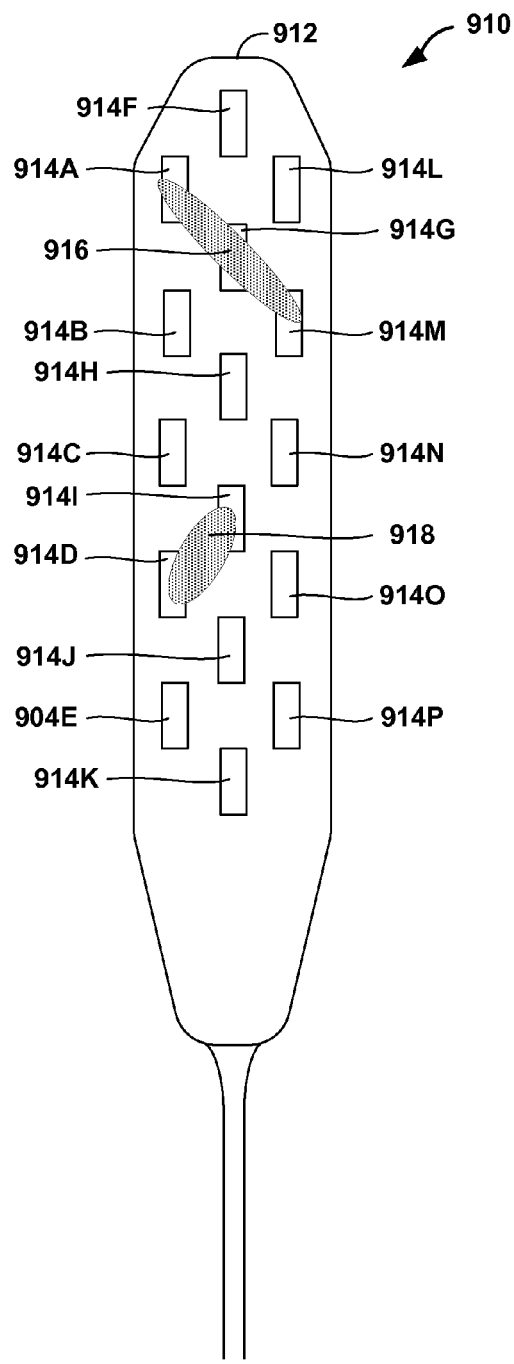

FIGS. 21A-21B are schematic diagrams illustrating top views of example paddle leads having a plurality of electrodes positioned on at least one surface of the paddle lead. In FIG. 21A, paddle lead 900 has an elongated lead body 902 that carries a two-dimensional array of electrodes 904A-904P (collectively referred to as "electrodes 904") on its top surface. A two-dimensional array generally refers to an ordering of electrodes along at least two different lines, e.g., as rows and columns. Electrodes 904 are arranged in "2×8" configuration, due to its 2 column, 8 row layout.

Programmer 40 and, in particular, processor 53 has recruited electrodes 904B, 904C, 904J, and 904K to produce stimulation zone 906. Also, processor 53 has recruited electrodes 904G and 904O to produce anodal or shielding zone 908.

In FIG. 21B, paddle lead 910 has an elongated lead body 912 that carries an array of electrodes 914A-914P (collectively referred to as "electrodes 914") on its top surface. Electrodes 914 are arranged in "5×6×5" configuration, due to the number of electrodes in each of its 3 columns.

Programmer 40 and, in particular, processor 53 has recruited electrodes 914A, 914G, and 914M to produce stimulation zone 916. Also, processor 53 has recruited electrodes 914D and 914I to produce anodal or shielding zone 918.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various aspects of the disclosure have been described. These and other aspects are within the scope of the following claims.

The invention claimed is:

1. A programmer for an implantable electrical stimulator, the programmer comprising:
   a user interface that displays a graphical representation of at least one electrical stimulation zone and receives user input graphically manipulating at least one of a size and a shape of the representation of the at least one electrical stimulation zone; and
   a processor configured to define a program to control delivery of electrical stimulation therapy by the implantable electrical stimulator based on the user input, wherein the processor is configured to:
      define an intensity of the at least one electrical stimulation zone;
      define each of a plurality of electrodes, on at least one lead, to deliver at least a portion of the electrical stimulation therapy;
      automatically determine an electrical stimulation contribution of each of the plurality of defined electrodes to the at least one stimulation zone; and
      automatically determine a stimulation amplitude of the portion of the electrical stimulation therapy delivered by each of the plurality of defined electrodes based on the electrical stimulation contribution of the electrode and the intensity of the at least one electrical stimulation zone, wherein the amplitude of at least one of the plurality of defined electrodes is equal to an amplitude corresponding to the intensity of the at least one electrical stimulation zone, and wherein a sum of the amplitudes of the plurality of defined electrodes is greater than the amplitude corresponding to the intensity of the at least one electrical stimulation zone.

2. The programmer of claim 1, wherein the user input comprises stretching the representation of the at least one stimulation zone.

3. The programmer of claim 1, wherein the user input further comprises moving the representation of the at least one stimulation zone from a first location on a display to a second location on the display.

4. The programmer of claim 1, wherein the user interface further receives user input that defines the intensity of the at least one electrical stimulation zone.

5. The programmer of claim 1, wherein the processor is configured to control at least one of a rate of change of a stretch of the at least one stimulation zone and a rate of change of a move of the at least one stimulation zone.

6. The programmer of claim 1, wherein the processor is further configured to:
   generate an electrical stimulation amplitude to be delivered by an electrode carried by a housing of the implantable electrical stimulator based on a sum of the electrical stimulation amplitudes of the plurality of defined electrodes.

7. The programmer of claim 6, wherein the processor is further configured to:
   modify the electrical stimulation amplitude to be delivered by the electrode carried by the housing of the implantable electrical stimulator in response to at least one of the user interface receiving user input graphically defining a representation of another electrical stimulation zone, the at least one electrical stimulation zone moving, and the at least one electrical stimulation zone stretching.

8. The programmer of claim 1, wherein the processor is further configured to:
   compare the determined electrical stimulation contribution of each of the plurality of defined electrodes to a threshold value; and
   determine whether each of the plurality of defined electrodes will be used to deliver at least a portion of the electrical stimulation therapy based on the comparison.

9. The programmer of claim 1, wherein the processor is further configured to:
   generate and display to a user an indication of zone extent based upon at least one of the defined electrodes.

10. The programmer of claim 9, wherein the indication of zone extent displayed to the user provides a visual indication of a relative electrical stimulation contribution of the at least one of the defined electrodes to the at least one stimulation zone.

11. The programmer of claim 1, wherein the user interface further receives at least one of user input that moves the representation of the at least one electrical stimulation zone, and user input that stretches the representation of the at least one electrical stimulation zone.

12. The programmer of claim 1, wherein at least two of the plurality of defined electrodes are the same polarity.

13. The programmer of claim 1, wherein the processor is further configured to multiply the electrical stimulation contribution by the amplitude corresponding to the intensity of the at least one electrical stimulation zone to determine the stimulation amplitude of each of the plurality of electrodes within the at least one stimulation zone, wherein the electrode stimulation contribution of at least one of the plurality of defined electrodes is 1.0, and wherein the electrode contribution of a second of the plurality of defined electrodes is greater than 0.0 and less than 1.0.

14. The programmer of claim 1, wherein the processor is further configured to control an implantable medical device to deliver stimulation with the plurality of defined electrodes based on the defined stimulation amplitudes.

15. A method comprising:
   receiving, via a programmer device for an electrical stimulator, user input that graphically manipulates at least one of a size and a shape of a graphical representation of at least one electrical stimulation zone displayed on the programmer;
   defining an intensity of the at least one electrical stimulation zone; and defining a program to control delivery of electrical stimulation therapy based on the user input, wherein defining the program comprises:
  defining each of a plurality of electrodes, on at least one lead, to deliver at least a portion of the electrical stimulation therapy;
  automatically determining an electrical stimulation contribution of each of the plurality of defined electrodes to the at least one stimulation zone; and
  automatically determining a stimulation amplitude of the portion of the electrical stimulation therapy delivered by each of the plurality of defined electrodes based on the electrical stimulation contribution of the electrode and the intensity of the at least one electrical stimulation zone, wherein the amplitude of at least one of the plurality of defined electrodes is equal to an amplitude corresponding to the intensity of the at least one electrical stimulation zone, and wherein a sum of the amplitudes of the plurality of defined electrodes is greater than the amplitude corresponding to the intensity of the at least one electrical stimulation zone.

16. The method of claim 15, wherein the user input comprises stretching the representation of the at least one stimulation zone.

17. The method of claim 15, wherein the user input further comprises moving the representation of the at least one stimulation zone from a first location on a display to a second location on the display.

18. The method of claim 15, further comprising:
  receiving, via the programmer device, user input that defines the intensity of the at least one electrical stimulation zone.

19. The method of claim 15, further comprising:
  controlling at least one of a rate of change of a stretch of the at least one stimulation zone and a rate of change of a move of the at least one stimulation zone.

20. The method of claim 15, further comprising:
  generating an electrical stimulation amplitude to be delivered by an electrode carried by a housing of the electrical stimulator based on a sum of the electrical stimulation amplitudes of each of the plurality of defined electrodes.

21. The method of claim 20, further comprising:
  modifying, the electrical stimulation amplitude to be delivered by the electrode carried by the housing of the implantable electrical stimulator in response to at least one of the user interface receiving user input graphically defining a representation of another electrical stimulation zone, the at least one electrical stimulation zone moving, and the at least one electrical stimulation zone stretching.

22. The method of claim 15, further comprising:
  comparing the determined electrical stimulation contribution of each of the plurality of defined electrodes to a threshold value; and
  determining each of the plurality of defined electrodes will be used to deliver at least a portion of the electrical stimulation therapy based on the comparison.

23. The method of claim 15, further comprising:
  generating and displaying to a user an indication of zone extent based upon the at least one of the defined electrodes.

24. The method of claim 23, wherein the indication of zone extent displayed to the user provides a visual indication of a relative electrical stimulation contribution of the at least one defined electrode to the at least one stimulation zone.

25. The method of claim 15, further comprising:
  receiving, in the programmer device, at least one of user input that moves the representation of the at least one electrical stimulation zone and user input that stretches the representation of the at least one electrical stimulation zone.

26. The method of claim 15, wherein the at least two of the plurality of defined electrodes are the same polarity.

27. The method of claim 15, wherein the program further comprises multiplying the electrical stimulation contribution by the amplitude corresponding to the intensity of the at least one electrical stimulation zone to determine the stimulation amplitude of each of the plurality of defined electrodes within the at least one stimulation zone, wherein the electrode stimulation contribution of at least one of the plurality of defined electrodes is 1.0, and wherein the electrode contribution of a second of the plurality of defined electrodes is less than 1.0.

28. The method of claim 15, further comprising controlling an implantable medical device to deliver stimulation with the plurality of defined electrodes based on the defined stimulation amplitudes.

29. A programmer device for an electrical stimulator, the programmer device comprising:
  means for receiving, via the programmer device for the electrical stimulator, user input that graphically manipulates at least one of a size and a shape of a graphical representation of at least one electrical stimulation zone displayed on the programmer device;
  means for defining an intensity of the at least one electrical stimulation zone; and
  means for defining a program to control delivery of electrical stimulation therapy based on the user input, wherein the means for defining the program comprises:
    means for defining, each of a plurality of electrodes, on at least one lead, to deliver at least a portion of the electrical stimulation therapy;
    means for automatically determining, an electrical stimulation contribution of each of the plurality of defined electrodes to the at least one stimulation zone; and
    means for automatically determining a stimulation amplitude of the portion of the electrical stimulation therapy delivered by each of the plurality of defined electrodes based on the electrical stimulation contribution of the electrode and the intensity of the at least one electrical stimulation zone, wherein the amplitude of at least one of the plurality of defined electrodes is equal to an amplitude corresponding to the intensity of the at least one electrical stimulation zone, and wherein a sum of the amplitudes of the plurality of defined electrodes is greater than the amplitude corresponding to the intensity of the at least one electrical stimulation zone.

30. The programmer device of claim 29, wherein the user input comprises stretching the representation of the at least one stimulation zone.

31. The programmer device of claim 29, wherein the user input further comprises moving the representation of the at least one stimulation zone from a first location on a display to a second location on the display.

32. The programmer device of claim 29, further comprising:
  means for receiving, via the programmer device, user input that defines the intensity of the at least one electrical stimulation zone.

33. The programmer device of claim 29, further comprising:

means for controlling at least one of a rate of change of a stretch of the at least one stimulation zone and a rate of change of a move of the at least one stimulation zone.

34. The programmer device of claim 29, further comprising:
means for generating, an electrical stimulation amplitude to be delivered by an electrode carried by a housing of the electrical stimulator based on the electrical stimulation amplitude generated by each of the plurality of defined electrodes.

35. The programmer device of claim 34, further comprising:
means for modifying, the electrical stimulation amplitude to be delivered by the electrode carried by the housing of the electrical stimulator in response to at least one of the user interface receiving user input graphically defining a representation of another electrical stimulation zone, the at least one electrical stimulation zone moving, and the at least one electrical stimulation zone stretching.

36. The programmer device of claim 29, further comprising:
means for comparing the determined electrical stimulation contribution each of the plurality of defined electrodes to a threshold value; and
means for determining each of the plurality of defined electrodes will be used to deliver at least a portion of the electrical stimulation therapy based on the comparison.

37. The programmer device of claim 29, further comprising: means for generating and displaying to a user an indication of zone extent based upon at least one of the defined electrodes.

38. The programmer device of claim 37, wherein the indication of zone extent displayed to the user provides a visual indication of a relative electrical stimulation contribution of the at least one of the defined electrodes to the at least one stimulation zone.

39. The programmer device of claim 29, wherein the user input comprises at least one of the user interface receiving user input moving the representation of the at least one electrical stimulation zone, and the user interface receiving user input stretching the representation of the at least one electrical stimulation zone.

40. The programming device of claim 29, further comprising means for multiplying the electrical stimulation contribution by the amplitude corresponding to the intensity of the at least one electrical stimulation zone to determine the stimulation amplitude of each of the plurality of defined electrodes within the at least one stimulation zone, wherein the electrode stimulation contribution of at least one of the plurality of defined electrodes is 1.0, and wherein the electrode contribution of a second of the plurality of defined electrodes is greater than 0.0 and less than 1.0.

41. The programming device of claim 29, further comprising
means for controlling an implantable medical device to deliver stimulation with the plurality of defined electrodes based on the defined stimulation amplitudes.

42. A non-transitory computer-readable medium comprising instructions that, upon execution, cause a processor in a programmer for an electrical stimulator to:
receive user input graphically manipulating at least one of a size and a shape of a graphical representation of the at least one electrical stimulation zone displayed on the programmer;
define an intensity of the at least one electrical stimulation zone; and
define a program to control delivery of electrical stimulation therapy based on the user input, wherein the instructions that cause the processor to define the program comprise instructions that cause the processor to:
define each of a plurality of electrodes, on at least one lead, to deliver at least a portion of the electrical stimulation therapy;
automatically determine an electrical stimulation contribution of each of the plurality of defined electrodes to the at least one stimulation zone; and
automatically determine a stimulation amplitude of the portion of the electrical stimulation therapy delivered by each of the plurality of defined electrodes based on the electrical stimulation contribution of the electrode and the intensity of the at least one electrical stimulation zone, wherein the amplitude of at least one of the plurality of defined electrodes is equal to an amplitude corresponding to the intensity of the at least one electrical stimulation zone, and wherein a sum of the amplitudes of the plurality of defined electrodes is greater than the amplitude corresponding to the intensity of the at least one electrical stimulation zone.

43. The computer-readable medium of claim 42, wherein the user input comprises stretching the representation of the at least one defined stimulation zone.

44. The computer-readable medium of claim 42, wherein the user input further comprises moving the representation of the at least one stimulation zone from a first location on a display to a second location on the display.

45. The computer-readable medium of claim 42, further comprising instructions that, upon execution, cause the processor to:
receive user input that defines the intensity of the at least one electrical stimulation zone.

46. The computer-readable medium of claim 42, further comprising instructions that, upon execution, cause the processor to:
control at least one of a rate of change of a stretch of the at least one stimulation zone and a rate of change of a move of the at least one stimulation zone.

47. The computer-readable medium of claim 42, further comprising instructions that, upon execution, cause the processor to:
generate an electrical stimulation amplitude to be delivered by an electrode carried by a housing of an implantable medical device (IMD) based on a sum of the electrical stimulation amplitudes generated each of the plurality of defined electrodes.

48. The computer-readable medium of claim 47, further comprising instructions that, upon execution, cause the processor to:
modify, the electrical stimulation amplitude to be delivered by the electrode carried by the housing of the IMD in response to at least one of the user interface receiving user input graphically defining a representation of another electrical stimulation zone, the at least one electrical stimulation zone moving, and the at least one electrical stimulation zone stretching.

49. The computer-readable medium of claim 42, further comprising instructions that, upon execution, cause the processor to:
receive at least one of user input that moves the representation of the at least one electrical stimulation zone and user input that stretches the representation of the at least one electrical stimulation zone.

50. The computer readable medium of claim 42, further comprising instructions that, upon execution, cause the processor to
multiply the electrical stimulation contribution by the amplitude corresponding to the intensity of the at least one electrical stimulation zone to determine the stimulation amplitude of each of the plurality of defined electrodes within the at least one stimulation zone, wherein the electrode stimulation contribution of at least one of the plurality of defined electrodes is 1.0, and wherein the electrode contribution of a second of the plurality of defined electrodes greater than 0.0 and less than 1.0.

51. The computer readable medium of claim 42, further comprising instructions that, upon execution, cause the processor to
control an implantable medical device to deliver stimulation with the plurality of defined electrodes based on the defined stimulation amplitudes.

52. A system comprising:
an implantable medical device (IMD) configured to deliver electrical stimulation therapy to a patient;
a user interface that displays a graphical representation of at least one electrical stimulation zone and receives user input graphically manipulating at least one of a size and a shape of the representation of the at least one electrical stimulation zone; and
a processor configured to define a program to control delivery of electrical stimulation therapy by a stimulator based on the user input, wherein the processor is further configured to:
define an intensity of the at least one electrical stimulation zone
define each of a plurality of electrodes, on at least one lead, to deliver at least a portion of the electrical stimulation therapy;
automatically determine an electrical stimulation contribution of each of the plurality of defined electrodes to the at least one stimulation zone; and
automatically determine a stimulation amplitude of the portion of the electrical stimulation therapy delivered by each of the plurality of defined electrodes based on the electrical stimulation contribution of the electrode and the intensity of the at least one electrical stimulation zone, wherein the amplitude of at least one of the plurality of defined electrodes is equal to an amplitude corresponding to the intensity of the at least one electrical stimulation zone, and wherein a sum of the amplitudes of the plurality of defined electrodes is greater than the amplitude corresponding to the intensity of the at least one electrical stimulation zone.

53. The system of claim 52, further comprising a programmer device for programming the IMD that includes the user interface and the processor.

54. The system of claim 52, wherein the user input comprises at least one of stretching the representation of the at least one stimulation zone and moving the representation of the at least one stimulation zone from a first location on a display to a second location on the display.

55. The system of claim 52, wherein the user interface further receives user input that defines the intensity of the at least one electrical stimulation zone.

56. The system of claim 52, wherein the processor is configured to control at least one of a rate of change of a stretch of the at least one stimulation zone and a rate of change of a move of the at least one stimulation zone.

57. The system of claim 52, wherein the processor is further configured to:
generate, an electrical stimulation amplitude to be delivered by an electrode carried by a housing of the IMD based on the electrical stimulation amplitude generated by each of the plurality of defined electrodes.

58. The system of claim 57, wherein the processor is further configured to:
modify, the electrical stimulation amplitude to be delivered by the electrode carried by the housing of the IMD in response to at least one of the user interface receiving user input graphically defining a representation of another electrical stimulation zone, the at least one electrical stimulation zone moving, and the at least one electrical stimulation zone stretching.

59. The system of claim 57, wherein the processor is further configured to:
compare the determined electrical stimulation contribution of each of the plurality of defined electrodes to a threshold value; and
determine whether each of the plurality of defined electrodes will be used to deliver at least a portion of the electrical stimulation therapy based on the comparison.

60. The system of claim 57, wherein the processor is further configured to:
generate and display to a user an indication of zone extent based upon at least one of the defined electrodes.

61. The system of claim 60, wherein the indication of zone extent displayed to the user provides a visual indication of a relative electrical stimulation contribution of the at least one of the defined electrodes to the at least one stimulation zone.

62. The system of claim 52, wherein the processor is further configured to
multiply the electrical stimulation contribution by the amplitude corresponding to the intensity of the at least one electrical stimulation zone to determine the stimulation amplitude of each of the plurality of defined electrodes within the at least one stimulation zone, wherein the electrode stimulation contribution of at least one of the plurality of defined electrodes is 1.0, and wherein the electrode contribution of a second of the plurality of defined electrodes is greater than 0.0 and less than 1.0.

63. The system of claim 52, wherein the processor is further configured to
control the IMD to deliver stimulation with the plurality of defined electrodes based on the defined stimulation amplitudes.

* * * * *